United States Patent
Jang et al.

(10) Patent No.: US 6,395,471 B1
(45) Date of Patent: May 28, 2002

(54) HEPATITIS C SURROGATE VIRUS FOR TESTING THE ACTIVITY OF HEPATITIS C VIRUS PROTEASE, A RECOMBINANT GENE AND A USE THEREOF

(75) Inventors: Sung Key Jang; Bumsuk Hahm, both of Pohang (KR)

(73) Assignee: LG Chemicals Co. Ltd. (KR)

( * ) Notice: Subject to any disclaimer, the term of this patent is extended or adjusted under 35 U.S.C. 154(b) by 0 days.

(21) Appl. No.: 09/202,904
(22) PCT Filed: Jun. 25, 1997
(86) PCT No.: PCT/KR97/00120
§ 371 (c)(1),
(2), (4) Date: Dec. 23, 1998
(87) PCT Pub. No.: WO98/00548
PCT Pub. Date: Jan. 8, 1998

(30) Foreign Application Priority Data

Jun. 28, 1996 (KR) .............................. 96-24910

(51) Int. Cl.⁷ ........................... C12Q 1/70; C12N 7/01; C07H 21/00
(52) U.S. Cl. ............................. 435/5; 435/23; 435/24; 435/235.1; 536/23.2; 536/23.4; 536/23.72
(58) Field of Search ................... 435/5, 23, 24, 435/235.1; 536/23.2, 23.4, 23.72

(56) References Cited

FOREIGN PATENT DOCUMENTS

WO    WO9208734    5/1992

OTHER PUBLICATIONS

Filocamo et al., Chimeric Sindbis Viruses Dependent on the NS3 Protease of Hepatitis C Virus, Journal of Virology 71(2):1417–427, 1997.*
Patent Abstracts of Japan, vol. 16, No. 419 (C–981), 1992, Kokai No. 4–144 686 (Kunitada Shimotoono).
Hahm et al., 1996, "Generation of a novel poliovirus with a requirement of hepatitis C virus protease NS3 activity" Virology 226:318–326.

* cited by examiner

*Primary Examiner*—Donna C. Wortman
(74) *Attorney, Agent, or Firm*—Baker Botts LLP

(57) ABSTRACT

The present invention provides a hybrid virus comprising poliovirus and the hepatitis C virus protease NS3 and a target site for NS3. The hybrid virus is useful for screening for drugs against hepatitis C virus.

6 Claims, 12 Drawing Sheets

FIG. 2 vNS3ΔC-PV1

PV1

FIG. 6A

Figure 1:
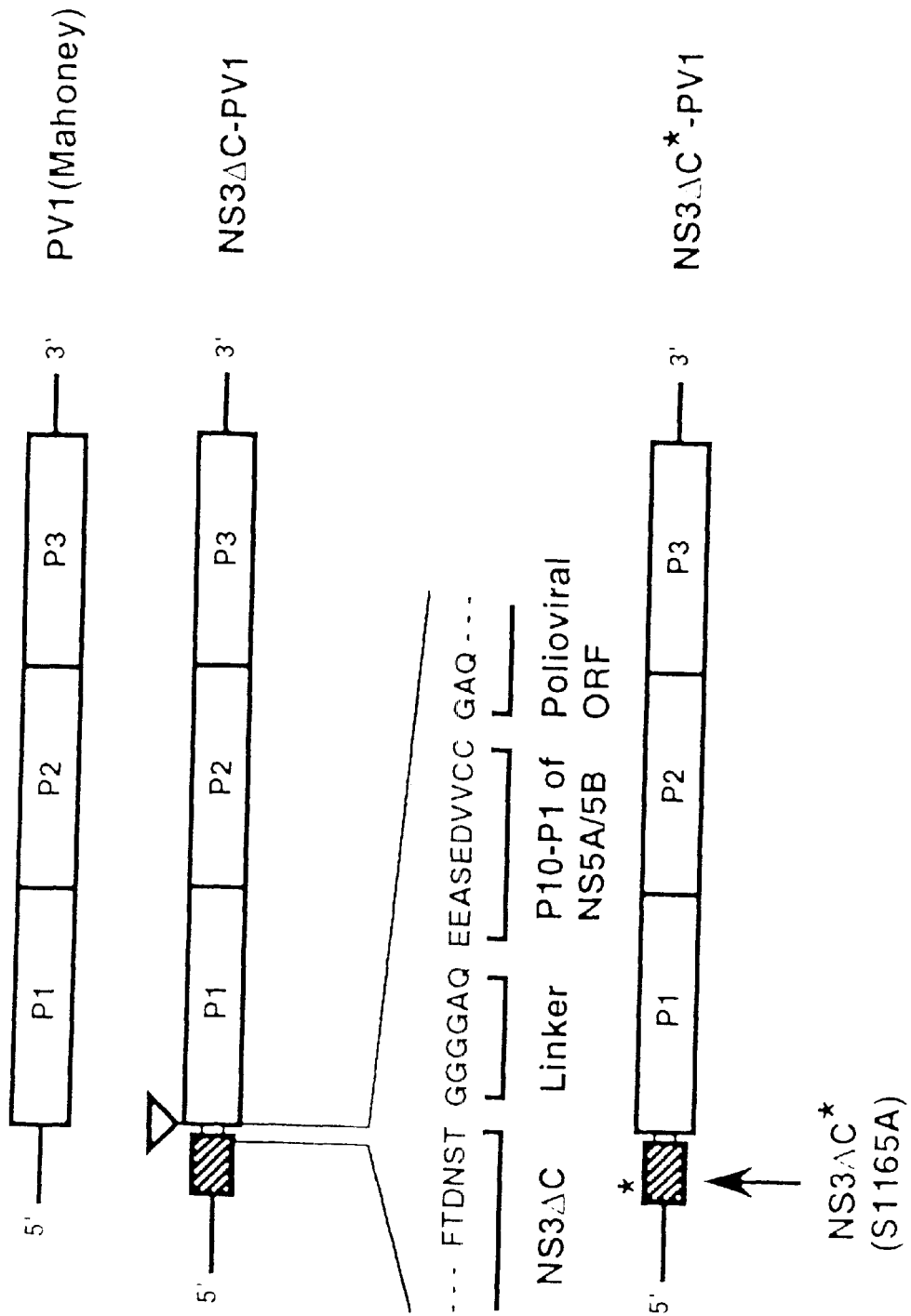
Figure 3:
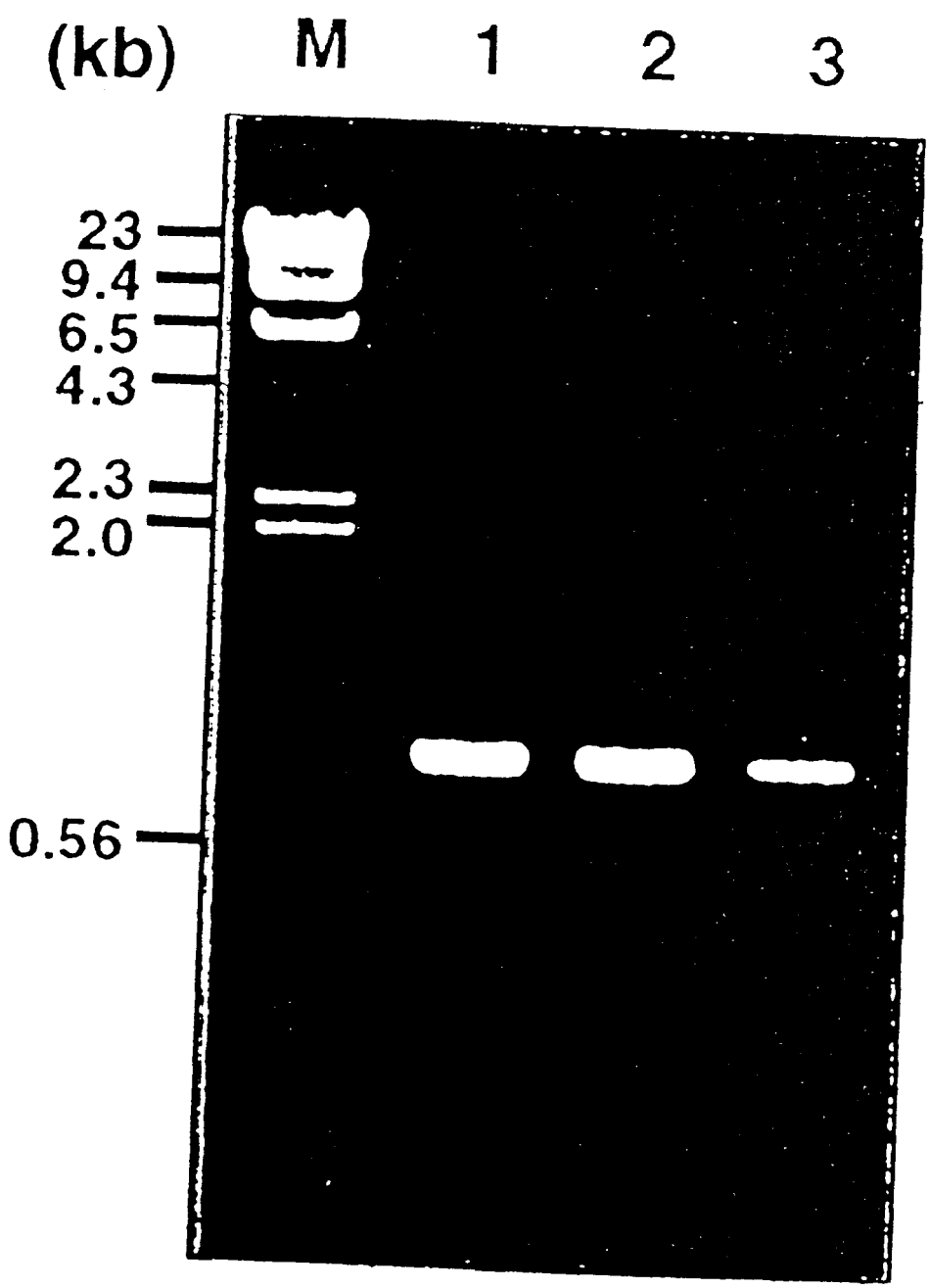
Figure 4A:
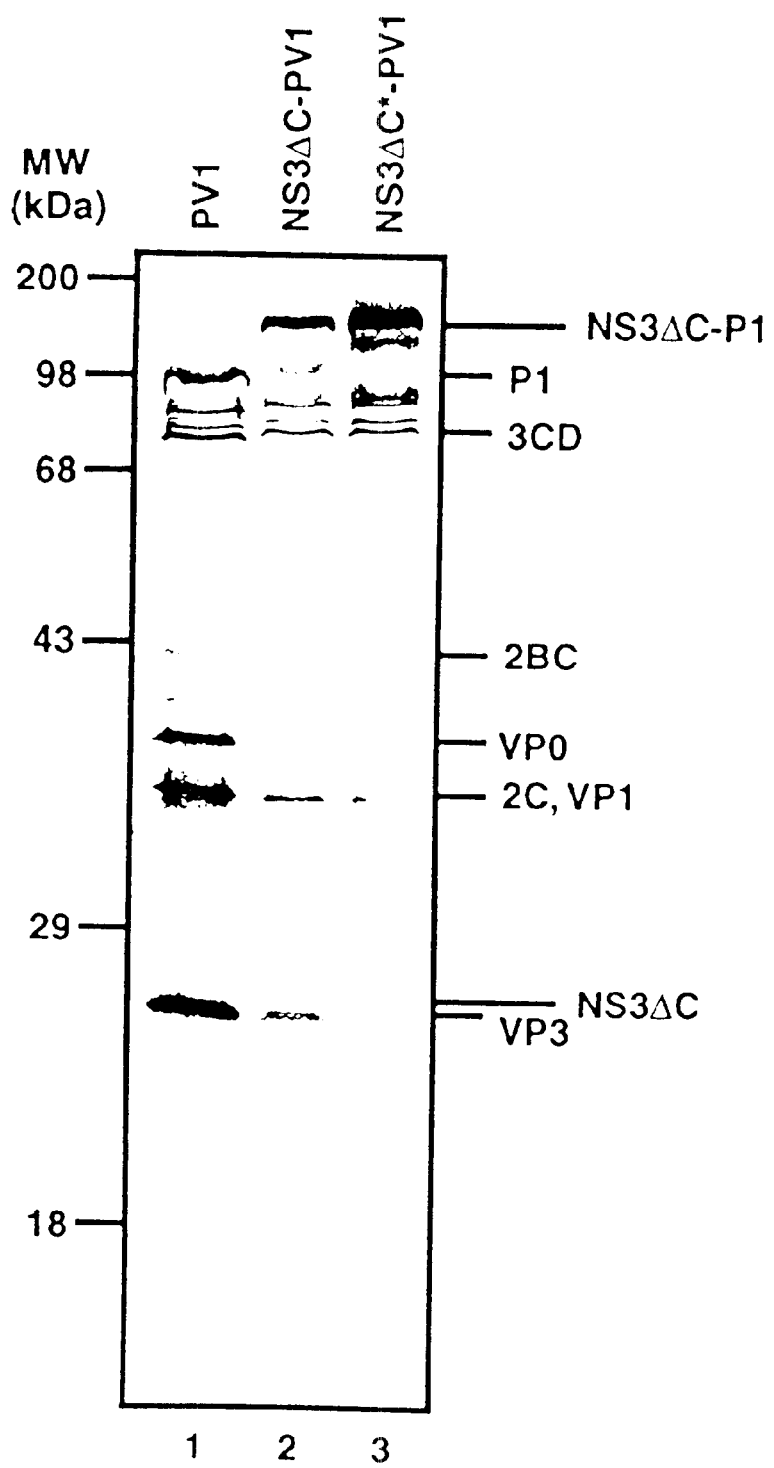
Figure 4B:
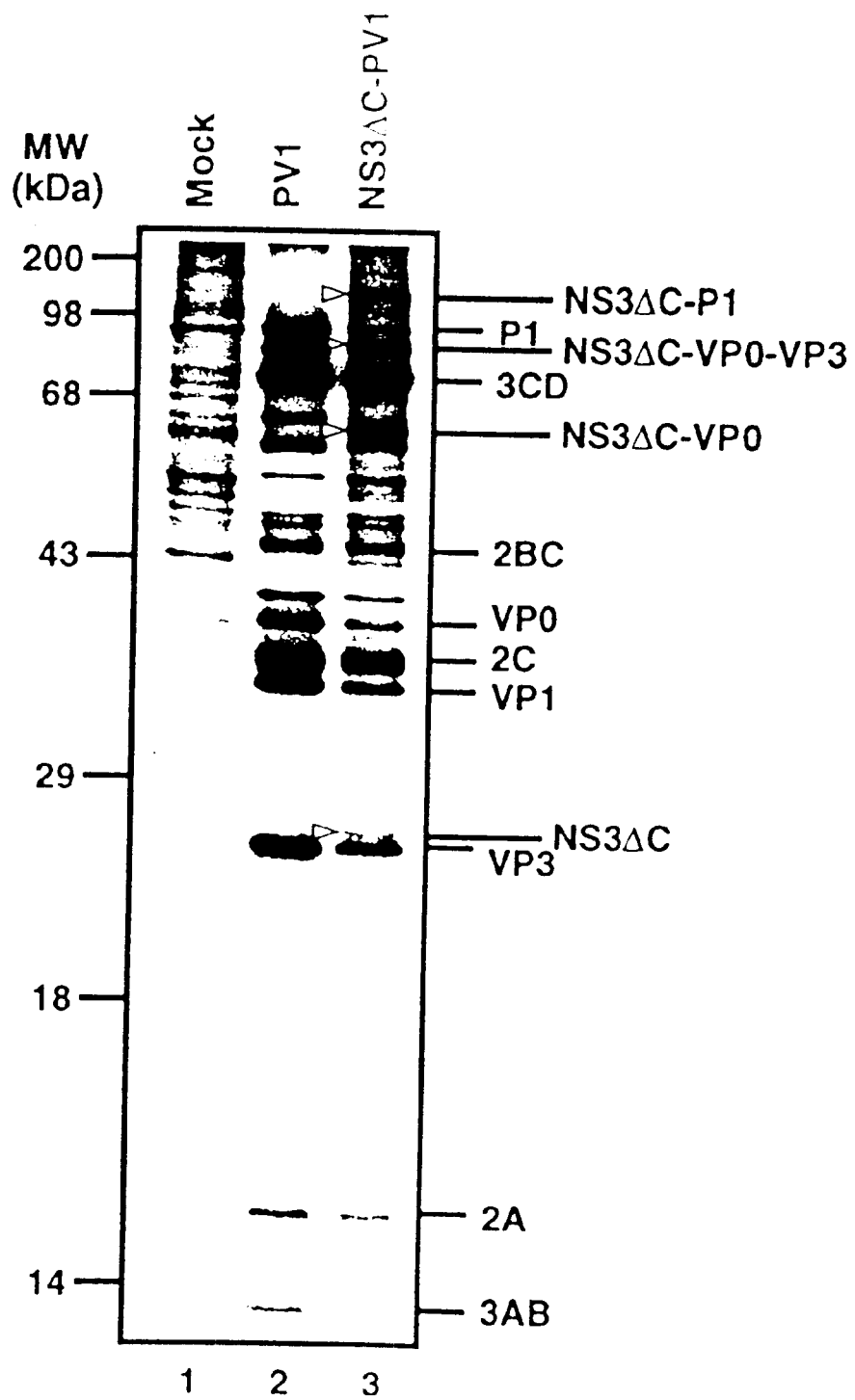
Figure 4C:
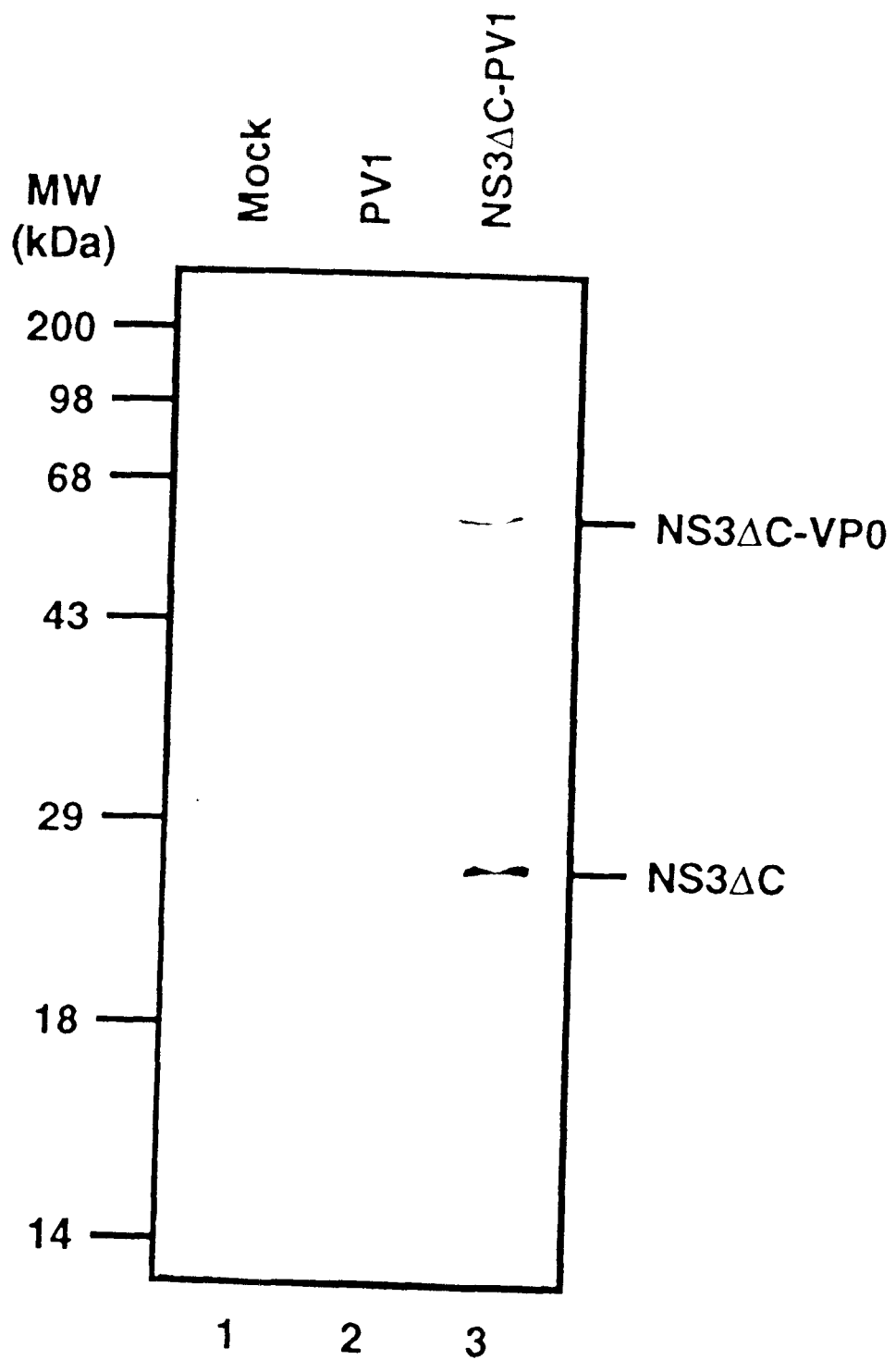

```
TTAAAACAGCTCTGGGGTTGTACCCACCCCAGAGGCCCACGTGGCGGCTAGTACTCCGGT
ATTGCGGTACCCTTGTACGC
CTGTTTTATACTCCCTTCCCGTAACTTAGACGCACAAAACCAAGTTCAATAGAAGGGGG
TACAAACCAGTACCACCACGA
ACAAGCACTTCTGTTTCCCCGGTGATGTCGTATAGACTGCTTGCGTGGTTGAAAGCGACG
GATCCGTTATCCGCTTATGT
ACTTCGAGAAGCCCAGTACCACCTCGGAATCTTCGATGCGTTGCGCTCAGCACTCAACCC
CAGAGTGTAGCTTAGGCTGA
TGAGTCTGGACATCCCTCACCGGTGACGGTGGTCCAGGCTGCGTTGGCGGCCTACCTATG
GCTAACGCCATGGACGCTA
GTTGTGAACAAGGTGTGAAGAGCCTATTGAGCTACATAAGAATCCTCCGGCCCTGAAT
GCGGCTAATCCCAACCTCGGA
GCAGGTGGTCACAAACCAGTGATTGGCCTGTCGTAACGCGCAAGTCCGTGGCGGAACCA
CTACTTTGGGTGTCCGTGTT
TCCTTTTATTTTATTGTGGCTGCTTATGGTGACAATCACAGATTGTTATCATAAAGCGA
AGACGGTATAGCTTGATATCG
AATTCCGGGATCCTCTAGCATGGCCAGTCATCATCATCATCATGGAATTGTCGAC
AATTCCCCGGCCGATAGCCTT
GAAGGGCAGGGGTGGCAACTCCCCGCTCCCATCACGGCCTACTCCCAACAGACGCGGGCC
TACTTGGTTGCATCATCAC
TAGCCTCACAGGCCGGGACAAGAACCAAGTCGAGGGGAGGTTCAAGTGGTTTCCACCGC
AACACAATCTTTCCTGGCGA
CCTGCGTCAATGGCGCTTGGACTGTCTTCCATGGTGCCGGCTCAAAGACCCTAGCCGGCC
AAAGGGGCCAATTACCCAA
ATGTACACCAATGTAGACCTGGACCTCGTCGGCTGGCAGGCACCCCCGGGTCGCGTCCCC
TGACACCATGCACCTGCGG
CAGCTCAGACCTTTACTTGGTCACGAGACATGCTGATGTCATTCCGGTGCGCCGGCGGGG
CGACAGTAGGGGGAGCCTAC
CCTCTCCCAGACCAGTCTCCTACTTGAAGGGCTCCTCGGGTGGTCCACTGCTCTGCCCTTC
GGGGCACGCTGTTGGCATC
TTTCGGGCTGCTGTATGCACCCGGGGGGTTGCGAAGGCGGTGGACTTCATACCCGTTGAA
TCTATGGAAACTACTATGCG
GTCTCCGGTCTTCACAGATAACTCAACCGGAGGAGGAGGCGCGCAAGAGGAAGCCAGTGA
GGACGTCGTCTGCTGCGGAG
CTCAGGTTTCATCACAGAAAGTGGGCGCACATGAAAACTCAAATAGAGCGTATGGTGGT
TCTACCATTAATTACACCACC
ATTAATTATTATAGAGATTCAGCTAGTAACGCGGCTTCGAAACAGGACTTCTCTCAAGA
CCCTTCCAAGTTCACCGAGCC
CATCAAGGATGTCCTGATAAAAACAGCCCCAATGCTAAACTCGCCAAACATAGAGGCTT
GCGGGTATAGCGATAGAGTAC
TGCAATTAACACTGGGAAACTCCACTATAACCACACAGGAGGCGGCTAATTCAGTAGTC
GCTTATGGGCGTTGGCCTGAA
TATCTGAGGGACAGCGAAGCCAATCCAGTGGACCAGCCGACAGAACCAGACGTCGCTGCA
TGCAGGTTTTATACGCTAGA
CACCGTGTCTTGGACGAAAGAGTCGCGAGGGTGGTGGTGGAAGTTGCCTGATGCACTGAG
GGACATGGGACTCTTTGGGC
AAAATATGTACTACCACTACCTAGGTAGGTCCGGGTACACCGTGCATGTACAGTGTAAC
GCCTCCAAATTCCACCAGGGG
GCACTAGGGGTATTCGCCGTACCAGAGATGTGTCTGGCCGGGGATAGCAACACCACTACC
ATGCACACCAGCTATCAAAA
TGCCAATCCTGGCGAGAAGGAGGCACTTTCACGGGTACGTTCACTCCTGACAACAACCA
GACATCACCTGCCCGCAGGT
TCTGCCCGGTGGATTACCTCCTTGGAAATGGCACGTTGTTGGGGAATGCCTTTGTGTTCC
CGCACCAGATAATAAACCTA
CGGACCAACAACTGTGCTACACTGGTACTCCCTTACGTGAACTCCCTCTCGATAGATAGT
ATGGTAAAGCACAATAATTG
GGGAATTGCAATATTACCATTGGCCCCATTAAATTTTGCTAGTGAGTCCTCCCCAGAGA
TTCCAATCACCTTGACCATAG
```

FIG. 6B

```
CCCCTATGTGCTGTGAGTTCAATGGATTAAGAAACATCACCCTGCCACGCTTACAGGGCC
TGCCGGTCATGAACACCCCT
GGTAGCAATCAATATCTTACTGCAGACAACTTCCAGTCACCGTGTGCGCTGCCTGAATT
TGATGTGACCCCACCTATTGA
CATACCCGGTGAAGTAAAGAACATGATGGAATTGGCAGAAATCGACACCATGATTCCCT
TTGACTTAAGTGCCACAAAAA
AGAACACCATGGAAATGTATAGGGTTCGGTTAAGTGACAAACCACATACAGACGATCCC
ATACTCTGCCTGTCACTCTCT
CCAGCTTCAGATCCTAGGTTGTCACATACTATGCTTGGAGAAATCCTAAATTACTACAC
ACACTGGGCAGGATCCCTGAA
GTTCACGTTTCTGTTCTGTGGATCCATGATGGCAACTGGCAAACTGTTGGTGTCATACG
CGCCTCCTGGAGCCGACCCAC
CAAAGAAGCGTAAGGAGGCGATGTTGGGAACACATGTGATCTGGGACATAGGACTGCAG
TCCTCATGTACTATGGTAGTG
CCATGGATTAGCAACACCACGTATCGGCAAACCATAGATGATAGTTTCACCGAAGGCGG
ATACATCAGCGTCTTCTACCA
AACTAGAATAGTCGTCCCTCTTTCGACACCCAGAGAGATGGACATCCTTGGTTTTGTGT
CAGCGTGTAATGACTTCAGCG
TGCGCTTGTTGCGAGATACCACACATATAGAGCAAAAGCGCTAGCACAGGGGTTAGGT
CAGATGCTTGAAAGCATGATT
GACAACACAGTCCGTGAAACGGTGGGGGCGGCAACATCTAGAGACGCTCTCCCAAACACT
GAAGCCAGTGGACCAACACA
CTCCAAGGAAATTCCGGCACTCACCGCAGTGGAAACTGGGGCCACAAATCCACTAGTCCC
TTCTGATACAGTGCAAACCA
GACATGTTGTACAACATAGGTCAAGGTCAGAGTCTAGCATAGAGTCTTTCTTCGCGCGG
GGTGCATGCGTGACCATTATG
ACCGTGGATAACCCAGCTTCCACCACGAATAAGGATAAGCTTTTTGCAGTGTGGAAGAT
CACTTATAAAGATACTGTCCA
GTTACGGAGGAAATTGGAGTTCTTCACCTATTCTAGATTTGATATGGAACTTACCTTTG
TGGTTACTGCAAATTTCACTG
AGACTAACAATGGCCATGCATTAAATCAAGTGTACCAAATTATGTACGTACCACCAGGC
GCTCCAGTGCCCGAAAAATGG
GACGACTACACATGGCAAACCTCATCAAATCCATCAATCTTTTACACCTACGGGACAGCT
CCAGCCCGGATCTCGGTACC
GTATGTTGGTATTTCGAACGCCTATTCACACTTTTACGACGGTTTTTCCAAAGTACCAC
TGAAGGACCAGTCGGCAGCAC
TAGGTGACTCCCTTTATGGTGCAGCATCTCTAAATGACTTCGGTATTTTGGCTGTTAGA
GTAGTCAATGATCACAACCCG
ACCAAGGTCACCTCCAAAATCAGAGTGTATCTAAAACCCAAACACATCAGAGTCTGGTG
CCCGCGTCCACCGAGGGCAGT
GGCGTACTACGGCCTGGAGTGGATTACAAGGATGGTACGCTTACACCCCTCTCCACCAA
GGATCTGACCACATATGGAT
TCGACACCAAAACAAAGCGGTGTACACTGCAGGTTACAAAATTTGCAACTACCACTTG
GCCACTCAGGATGATTTGCAA
AACGCAGTGAACGTCATGTGGAGTAGAGACCTCTTAGTCACAGAATCAAGAGCCCAGGG
CACCGATTCAATCGCAAGGTG
CAATTGCAACGCAGGGGTGTACTACTGCGAGTCTAGAAGGAAATACTACCCAGTATCCT
TCGTTGGCCCAACGTTCCAGT
ACATGGAGGCTAATAACTATTACCCAGCTAGGTACCAGTCCCATATGCTCATTGGCCAT
GGATTCGCATCTCCAGGGGAT
TGTGGTGGCATACTCAGATGTCACCACGGGTGATAGGGATCATTACTGCTGGTGGAGA
AGGGTTGGTTGCATTTTCAGA
CATTAGAGACTTGTATGCCTACGAAGAAGAAGCCATGGAACAAGGCCTCACCAATTACA
TAGAGTCACTTGGGGCCGCAT
TTGGAAGTGGATTTACTCAGCAGATTAGCGACAAAATAACAGAGTTGACCAATATGGTG
ACCAGTACCATCACTGAAAAG
CTACTTAAGAACTTGATCAAGATCATATCCTCACTAGTTATTATAACTAGGAACTATGA
AGACACCACAACAGTGCTCGC
```

FIG. 6C

```
TACCCTGGCCCTTCTTGGGTGTGATGCTTCACCATGGCAGTGGCTTAGAAAGAAAGCATG
CGATGTTCTGGAGATACCTT
ATGTCATCAAGCAAGGTGACAGTTGGTTGAAGAAGTTTACTGAAGCATGCAACGCAGCT
AAGGGCCTGGAGTGGGTGTCA
AACAAAATCTCAAAATTCATTGATTGGCTCAAGGAGAAAATTATCCCACAAGCTAGAGA
TAAGTTGGAATTTGTAACAAA
ACTTAGACAACTAGAAATGCTGGAAAACCAAATCTCAACTATACACCAATCATGCCCTA
GTCAGGAACACCAGGAAATTC
TATTCAATAATGTCAGATGGTTATCCATCCAGTCTAAGAGGTTTGCCCCTCTTTACGCA
GTGGAAGCCAAAAGAATACAG
AAACTCGAGCATACTATTAACAACTACATACAGTTCAAGAGCAAACACCGTATTGAACC
AGTATGTTTGCTAGTACATGG
CAGCCCCGGAACAGGTAAATCTGTAGCAACCAACCTGATTGCTAGAGCCATAGCTGAAA
GAGAAAACACGTCCACGTACT
CGCTACCCCCGGATCCATCACACTTCGACGGATACAAACAACAGGGAGTGGTGATTATGG
ACGACCTGAATCAAAACCCA
GATGGTGCGGACATGAAGCTGTTCTGTCAGATGGTATCAACAGTGGAGTTTATACCACC
CATGGCATCCCTGGAGGAGAA
AGGAATCCTGTTTACTTCAAATTACGTTCTAGCATCCACAAACTCAAGCAGAATTTCCC
CCCCCACTGTGGCACACAGTG
ACGCGTTAGCCAGGCGCTTTGCGTTCGACATGGACATTCAGGTCATGAATGAGTATTCT
AGAGATGGGAAATTGAACATG
GCCATGGCTACTGAAATGTGTAAGAACTGTCACCAACCAGCAAACTTTAAGAGATGCTG
TCCTTTAGTGTGTGGTAAGGC
AATTCAATTAATGGACAAATCTTCCAGAGTTAGATACAGTATTGACCAGATCACTACAA
TGATTATCAATGAGAGAAACA
GAAGATCCAACATTGGCAATTGTATGGAGGCTTTGTTTCAAGGACCACTCCAGTATAAA
GACTTGAAAATTGACATCAAG
ACGAGTCCCCCTCCTGAATGTATCAATGACTTGCTCCAAGCAGTTGACTCCCAGGAGGTG
AGAGATTACTGTGAGAAGAA
GGGTTGGATAGTTAACATCACCAGCCAGGTTCAAACAGAAAGGAACATCAACAGGGCAA
TGACAATTCTACAAGCGGTGA
CAACCTTCGCCGCAGTGGCTGGAGTTGTCTATGTCATGTATAAACTGTTTGCTGGACACC
AGGGAGCATACACTGGTTTA
CCAAACAAAAAACCCAACGTGCCCACCATTCGGACAGCAAAGGTACAAGGACCAGGGTTC
GATTACGCAGTGGCTATGGC
TAAAAGAAACATTGTTACAGCAACTACTAGCAAGGGAGAGTTCACTATGTTAGGAGTCC
ACGACAACGTGGCTATTTTAC
CAACCCACGCTTCACCTGGTGAAAGCATTGTGATCGATGGCAAAGAAGTGGAGATCTTG
GATGCCAAAGCGCTCGAAGAT
CAAGCAGGAACCAATCTTGAAATCACTATAATCACTCTAAAGAGAAATGAAAAGTTCAG
AGACATTAGACCACATATACC
TACTCAAATCACTGAGACAAATGATGGAGTCTTGATCGTGAACACTAGCAAGTACCCCA
ATATGTATGTTCCTGTCGGTG
CTGTGACTGAACAGGGATATCTAAATCTCGGTGGGCGCCAAACTGCTCGTACTCTAATG
TACAACTTTCCAACCAGAGCA
GGACAGTGTGGTGGAGTCATCACATGTACTGGGAAAGTCATCGGGATGCATGTTGGTGG
GAACGGTTCACACGGGTTTGC
AGCGGCCCTGAAGCGATCATACTTCACTCAGAGTCAAGGTGAAATCCAGTGGATGAGAC
CTTCGAAGGAAGTGGGATATC
CAATCATAAATGCCCCGTCCAAAACCAAGCTTGAACCCAGTGCTTTCCACTATGTGTTTG
AAGGGGTGAAGGAACCAGCA
GTCCTCACTAAAAACGATCCCAGGCTTAAGACAGACTTTGAGGAGGCAATTTTCTCCAA
GTACGTGGGTAACAAAATTAC
TGAAGTGGATGAGTACATGAAAGAGGCAGTAGACCACTATGCTGGCCAGCTCATGTCAC
TAGACATCAACACAGAACAAA
TGTGCTTGGAGGATGCCATGTATGGCACTGATGGTCTAGAAGCACTTGATTTGTCCACC
AGTGCTGGCTACCCTTATGTA
```

FIG. 6D

```
GCAATGGGAAAGAAGAAGAGAGACATCTTGAACAAACAAACCAGAGACACTAAGGAAA
TGCAAAAACTGCTCGACACATA
TGGAATCAACCTCCCACTGGTGACTTATGTAAAGGATGAACTTAGATCCAAAACAAAGG
TTGAGCAGGGGAAATCCAGAT
TAATTGAAGCTTCTAGTTTGAATGACTCAGTGGCAATGAGAATGGCTTTTGGGAACCTA
TATGCTGCTTTTCACAAAAAC
CCAGGAGTGATAACAGGTTCAGCAGTGGGGTGCGATCCAGATTTGTTTTGGAGCAAAAT
TCCGGTATTGATGGAAGAGAA
GCTGTTTGCTTTTGACTACACAGGGTATGATGCATCTCTCAGCCCTGCTTGGTTCGAGGC
ACTAAAGATGGTGCTTGAGA
AAATCGGATTCGGAGACAGAGTTGACTACATCGACTACCTAAACCACTCACACCACCTGT
ACAAGAATAAAACATACTGT
GTCAAGGGCGGTATGCCATCTGGCTGCTCAGGCACTTCAATTTTTAACTCAATGATTAA
CAACTTGATTATCAGGACACT
CTTACTGAAAACCTACAAGGGCATAGATTTAGACCACCTAAAAATGATTGCCTATGGTG
ATGATGTAATTGCTTCCTACC
CCCATGAAGTTGACGCTAGTCTCCTAGCCCAATCAGGAAAAGACTATGGACTAACTATG
ACTCCAGCTGACAAATCAGCT
ACATTTGAAACAGTCACATGGGAGAATGTAACATTCTTGAAGAGATTCTTCAGGGCAGA
CGAGAAATACCCATTTCTTAT
TCATCCAGTAATGCCAATGAAGGAAATTCATGAATCAATTAGATGGACTAAAGATCCTA
GGAACACTCAGGATCACGTTC
GCTCTCTGTGCCTTTTAGCTTGGCACAATGGCGAAGAAGAATATAACAAATTCCTAGCT
AAAATCAGGAGTGTGCCAATT
GGAAGAGCTTTATTGCTCCCAGAGTACTCAACATTGTACCGCCGTTGGCTTGACTCATT
TTAGTAACCCTACCTCAGTCG
AATGGATTGGGTCATACTGTTGTAGGGGTAAATTTTTCTTTAATTCGGAGGAAAAAA
AAAAAAAAAAAAAAAAAAAAA
AAAAAAAAAAAAAAAAAAAAAAAAAAAAAAAAAAAAAAAAAAAAAAAAAAAAAAACGGa
attAATTCTTGAAGACGAAAGGG
CCTCGTGATACGCCTATTTTTATAGGTTAATGTCATGATAATAATGGTTTCTTAGACGT
CAGGTGGCACTTTTCGGGGAA
ATGTGCGCGGAACCCCTATTTGTTTATTTTTCTAAATACATTCAAATATGTATCCGCTC
ATGAGACAATAACCCTGATAA
ATGCTTCAATAATATTGAAAAGGAAGAGTATGAGTATTCAACATTTCCGTGTCGCCCT
TATTCCCTTTTTTGCGGCATT
TTGCCTTCCTGTTTTGCTCACCCAGAAACGCTGGTGAAAGTAAAAGATGCTGAAGATC
AGTTGGGTGCACGAGTGGGTT
ACATCGAACTGGATCTCAACAGCGGTAAGATCCTTGAGAGTTTTCGCCCCGAAGAACGT
TTTCCAATGATGAGCACTTTT
AAAGTTCTGCTATGTGGCGCGGTATTATCCCGTGTTGACGCCGGGCAAGAGCAACTCGGT
CGCCGCATACACTATTCTCA
GAATGACTTGGTTGAGTACTCACCAGTCACAGAAAAGCATCTTACGGATGGCATGACAG
TAAGAGAATTATGCAGTGCTG
CCATAACCATGAGTGATAACACTGCGGCCAACTTACTTCTGACAACGATCGGAGGACCGA
AGGAGCTAACCGCTTTTTTG
CACAACATGGGGATCATGTAACTCGCCTTGATCGTTGGGAACCGGAGCTGAATGAAGCC
ATACCAAACGACGAGCGTGA
CACCACGATGCCTGCAGCAATGGCAACAACGTTGCGCAAACTATTAACTGGCGAACTACT
TACTCTAGCTTCCCGGCAAC
AATTAATAGACTGGATGGAGGCGGATAAAGTTGCAGGACCACTTCTGCGCTCGGCCCTT
CCGGCTGGCTGGTTTATTGCT
GATAAATCTGGAGCCGGTGAGCGTGGGTCTCGCGGTATCATTGCAGCACTGGGGCCAGAT
GGTAAGCCCTCCCGTATCGT
AGTTATCTACACGACGGGGAGTCAGGCAACTATGGATGAACGAAATAGACAGATCGCTG
AGATAGGTGCCTCACTGATTA
AGCATTGGTAACTGTCAGACCAAGTTTACTCATATATACTTTAGATTGATTTAAAACT
TCATTTTTAATTTAAAAGGATC
```

FIG. 6E

```
TAGGTGAAGATCCTTTTTGATAATCTCATGACCAAAATCCCTTAACGTGAGTTTTCGTT
CCACTGAGCGTCAGACCCCGT
AGAAAAGATCAAAGGATCTTCTTGAGATCCTTTTTTTCTGCGCGTAATCTGCTGCTTGC
AAACAAAAAAACCACCGCTAC
CAGCTGGTTTGTTTGCCGGATCAAGAGCTACCAACTCTTTTTCCGAAGGTAACTGGCTTC
AGCAGAGCGCAGATACCAAA
TACTGTCCTTCTAGTGTAGCCGTAGTTAGGCCACCACTTCAAGAACTCTGTAGCACCGCC
TACATACCTCGCTCTGCTAA
TCCTGTTACCAGTGGCTGCTGCCAGTGGCGATAAGTCGTGTCTTACCGGGTTGGACTCAA
GACGATAGTTACCGGATAAG
GCGCAGCGGTCGGGCTGAACGGGGGGTTCGTGCACACAGCCCAGCTTGGAGCGAACGACC
TACACCGAACTGAGATACCT
ACAGCGTGAGCATTGAGAAAGCGCCACGCTTCCCGAAGGGAGAAAGGCGGACAGGTATCC
GGTAAGCGGCAGGGTCGGAA
CAGGAGAGCGCACGAGGGAGCTTCCAGGGGGAAACGCCTGGTATCTTTATAGTCCTGTCG
GGTTTCGCCACCTCTGACTT
GAGCGTCGATTTTTGTGATGCTCGTCAGGGGGCGGAGCCTATGGAAAAACGCCAGCAAC
GCGGCCTTTTTACGGTTCCT
GGCCTTTTGCTGGCCTTTTGCTCACATGTTCTTTCCTGCGTTATCCCCTGATTCTGTGGA
TAACCGTATTACCGCCTTTG
AGTGAGCTGATACCGCTCGCCGCAGCCGAACGACCGAGCGCAGCGAGTCAGTGAGCGAGG
AAGCGGAAGAGCGCCTGATG
CGGTATTTTCTCCTTACGCATCTGTGCGGTATTTCACACCGCATATGGTGCACTCTCAGT
ACAATCTGCTCTGATGCCGC
ATAGTTAAGCCAGTATACACTCCGCTATCGCTACGTGACTGGGTCATGGCTGCGCCCGA
CACCCGCCAACACCCGCTGA
CGCGCCCTGACGGGCTTGTCTGCTCCCGGCATCCGCTTACAGACAAGCTGTGACCGTCTCC
GGGAGCTGCATGTGTCAGA
GGTTTTCACCGTCATCACCGAAACGCGCGAGGCAGCTGCGGTAAAGCTCATCAGCGTGGT
CGTGAAGCGATTCACAGATG
TCTGCCTGTTCATCCGCGTCCAGCTCGTTGAGTTTCTCCAGAAGCGTTAATGTCTGGCTT
CTGATAAAGCGGGCCATGTT
AAGGGCGGTTTTTTCCTGTTTGGTCACTTGATGCCTCCGTGTAAGGGGGAATTTCTGTT
CATGGGGGTAATGATACCGAT
GAAACGAGAGAGGATGCTCACGATACGGGTTACTGATGATGAACATGCCCGGTTACTGG
AACGTTGTGAGGGTAAACAAC
TGGCGGTATGGATGCGGCGGGACCAGAGAAAAATCACTCAGGGTCAATGCCAGCGCTTCG
TTAATACAGATGTAGGTGTT
CCACAGGGTAGCCAGCAGCATCCTGCGATGCAGATCCGGAACATAATGGTGCAGGGCGCT
GACTTCCGCGTTTCCAGACT
TTACGAAACACGGAAACCGAAGACCATTCATGTTGTTGCTCAGGTCGCAGACGTTTTGC
AGCAGCAGTCGCTTCACGTTC
GCTCGCGTATCGGTGATTCATTCTGCTAACCAGTAAGGCAACCCCGCCAGCCTAGCCGGG
TCCGCTCTCCCTTATGCGAC
TCCTGCATTAGGAAGCAGCCCAGTAGTAGGTTGAGGCCGTTGAGCACCGCCGCCGCAAGG
AATGGTGCATGCAAGGAGAT
GGCGCCCAACAGTCCCCCGGCCACGGGGCCTGCCACCATACCCACGCCGAAACAAGCGCTC
ATGAGCCCGAAGTGGCGAG
CCCGATCTTCCCCATCGGTGATGTCGGCGATATAGGCGCCAGCAACCGCACCTGTGGCGCC
GGTGATGCCGGCCACGATG
CGTCCGGCGTAGAGGATCCCGCGAAATTAATACGACTCACTATAGG
```

HEPATITIS C SURROGATE VIRUS FOR TESTING THE ACTIVITY OF HEPATITIS C VIRUS PROTEASE, A RECOMBINANT GENE AND A USE THEREOF

BACKGROUND OF THE INVENTION

1. Field of the Invention

The present invention relates to a hepatitis C virus (HCV), more particularly, is related to a hepatitis C surrogate virus which comprises poliovirus genome, HCV protease and its target site, and is suitable for testing efficacy of anti-HCV drugs and screening the same, a recombinant gene and a use thereof.

2. Description of the Related Arts

There are known some types of viruses which cause viral hepatitis. Hepatitis A virus is an RNA virus having a diameter of 27 mn and causing epidemic hepatitis through oral infection. Hepatitis B virus is a DNA virus having a diameter of 42 mn and causing hepatitis through blood infection. A hepatitis virus which does not belong to any of the above types was called non-A, non-B hepatitis virus.

Hepatitis C virus (HCV) is the major etiologic agent of non-A, non-B hepatitis (Alter et al, *N. Engl. J. Med.* 321, 1494–1500, 1989; Choo et al., *Science,* 244, 359–362, 1989; Kuo et al., *Science* 244, 362–364, 1989). This virus has been implicated in liver cirrhosis and hepatocellular carcinoma (Bruix et al., *Lancet* ii, 1004–1006, 1989; Saito et al., *Proc. Natl. Acad. Sci.* USA, 87, 6547–6549, 1990). At present, α-interferon is widely used for treating HCV patients. However, only about half of the patients respond to α-interferon, and about half of the responders suffer from a recurrence of the virus (Hino et al., C. J. *Med. Virol.,* 42, 299–305, 1994; Tsubota et al., *Hepatology,* 19, 1088–1094, 1994). Development of other anti-HCV drugs is, therefore, necessary.

In order to develop the anti-HCV drugs, it is essential to set up HCV cultivation system to test the efficacy of the drugs. However, in vitro cultivation systems available to date are inefficient and technically difficult to manipulate (Yoo et al., *J. Virol.,* 69, 32–38, 1995; Beach et al., Viral Hepatitis Research Foundation of Japan, 286, 67, 1993; Shimizu et al., *Proc. Natl. Acad. Sci.* USA, 89, 5477–5481, 1992). Furthermore, HCV titer is very low even in sera of hepatitis patients due to its nature of low yield. Accordingly, it is very difficult to screen or test for efficacy of antiviral drugs using HCV cultivation. Therefore, the surrogate virus will be very useful for studying HCV genes in virus replication and testing antiviral efficacy of drugs affecting HCV-encoded enzymes. Namely, the development of the surrogate virus for anti-HCV drugs is urgent.

SUMMARY OF THE INVENTION

Accordingly, the present invention is intended to overcome the above-mentioned disadvantage in the development of anti-HCV drugs and provide proper surrogate viruses for HCV suitable for the investigation of antiviral efficacy of drugs and proliferable in the HCV cultivation system.

An embodiment of the present invention is a recombinant gene coding hepatitis C surrogate virus comprising a virus gene coding picornavirus, a protease gene coding hepatitis C virus protease NS3 which is in an open reading frame (ORF) of said picornavirus, and a target gene coding target sites of said hepatitis C virus protease NS3 which is in said open reading frame of said picornavirus.

Among the picornaviruses, the poliovirus is preferred.

The target site is preferred to be selected from the group consisting of NS5A/5B, NS4A/4B and NS4B/5A.

The hepatitis C surrogate virus protease NS3 is preferred to cleave the peptide bond between cysteine of P1 and glycine of P1' as a target site.

In another aspect, the present invention provides a screening method of anti hepatitis C virus drugs comprising the step of detecting a material which inhibits surrogate virus proliferation expressed by the recombinant gene for coding hepatitis C surrogate virus.

In another aspect, the present invention provides a measuring method of anti-hepatitis C virus drugs activity comprising the steps of proliferating the surrogate virus expressed by the recombinant gene coding hepatitis C surrogate virus in the presence of anti-hepatitis C virus agents, and measuring the proliferating ability of the hepatitis C surrogate virus.

The present invention, in another aspect, provides a hepatitis C surrogate virus comprising the recombinant gene for coding hepatitis C surrogate virus.

The poliovirus's versatility is used in developing surrogate virus suitable for investigation of HCV protease activity.

HCV belongs to the family Flaviviridae whose members are enveloped viruses having a positive-sense RNA genome (Francki et al., *Arch. Virol* 2(Sullo.), 223, 1991; Inchauspe et al., *Proc. Natl. Acad, Sci.,* 88, 10292–10296, 1991; Miller et al., *Proc. Natl. Acad. Sci.,* 87, 2957–2061, 1990; Takamizawa et al., *J. Virol.* 65, 1105–1113, 1991). The RNA encodes a polyprotein (−3010 amino acids) with the following gene order: 5'-C'E1-E2-NS2-NS3-NS4A-NS4B-NS5A-NS5B-3'. During and/or after synthesis, the polyprotein is processed into functional proteins by host- and virus-encoded proteases. Core protein (C) and envelope proteins (E1 and E2) are believed to compose the structural elements of the virion particle. The balance of the processed proteins is believed to function in replication processes of the virus inside the host cells. The signal peptidase on the endoplasmic reticulum is responsible for the generation of the N-terminus of E1, E2, and possibly NS2. It has been suggested that the NS2/NS3 junction is cleaved by an HCV-encoded metalloprotease, which resides between the C-terminal portion of NS2 and the N-terminal region of NS3. The cleavage of the NS3/4A, NS4A/4B, NS4B/5A, and NS5A/5B sites depends on the activity of the serine protease NS3 (Bortenschlager et al., *J. Virol.* 68, 5045–5055, 1993; Eckart et al., *Biochem, Biophys. Res. Commun.* 192, 399–406, 1993; Grakoui et al., *J. Virol.* 67, 2832–2843, 1993; Han et al., *J. Gen. Virol.* 76, 985–993, 1995; Hijikata et al., *J. Virol.* 67, 4665–4675, 1993; Tomei et al., *J. Virol.* 67, 4017–4026, 1993). HCV protease NS3 is a good putative therapeutic target molecule for the development of anti-HCV drugs, since its activity is considered essential for viral proliferation. Protease activity of NS3 resides in the N-terminal part of NS3 (Bartenschlager et al., *J. Virol.* 67, 3835–3844, 1994; Han et al., *J. Gen Virol.* 76, 985–993, 1995; Lin et al., *J. Virol.* 68, 8147–8157, 1994), and NS4A enhances the protease activity of NS3 (Bartenschlager et al., *J. Virol.* 68, 3835–3844, 1994; Failla et al., *J. Virol.* 68, 3753–3760, 1994; Hahm et al., *J. Virol.* 69, 2534–2539, 1995; Lin et al., *J. Virol.* 69, 4373–4380, 1995; Tanji et al., *J. Virol.* 69, 1575–1581, 1995). Characterization of the NS3 protease using known protease inhibitors has revealed that NS3 is a chymotrypsin-like protease (Hahm et al., *J. Virol.* 69, 2534–2539, 1995).

The poliovirus is the prototype of picornaviruses. The polioviral genome is composed of a positive-sense RNA molecule that encodes a single open reading frame (ORF) (Kitamura et al., *Nature* (London) 291, 547–553, 1981; Racaniello et al., *Proc. Natl. Acad. Sci.* USA 78, 4887–4891, 1981). Upon infection, the genomic RNA is translated into a large precursor polyprotein via the internal ribosomal entry site (IRES) in the 5'-nontraslated region of the RNA (Jang et al., *J. Virol.* 62, 2636–2643, 1988; Pelletier et al., *Nature* (London) 334, 320–325, 1988; Pelletiet et al., *J. Virol.* 63, 441–444, 1989). The polyprotein, in turn, is processed into the mature viral structural and nonstructural proteins by the 2A, 3C, and 3CD proteases (Harris et al., *Semin. Virol.* 1, 323–333, 1991; Lawson and Semler., in "Current Topics in Microbiology and Immunology" (V.R. Racaniello, Ed.), 161, 49–87, 1990). Poliovirus is one of the best studied viruses and is relatively easy to manipulate and cultivate. Production of infectious poliovirus from cDNA clones has been practiced for a decade to study functions of poliovirus proteins (Molla et al., *Science* 254, 1647–1651, 1991; Van der Werf et al., *Proc. Natl. Acad. Sci. USA* 83, 2330–2334, 1986) or for use of the poliovirus as a vector in delivering foreign genes into host cells (Alexander et al., *Proc. Natl. Acad. Sci.* USA 91, 1406–1410, 1994; Andino et al., *Science* 265, 1448–1451, 1994; Lu et al., *J. Virol.* 69, 4797–4806, 1995)

Inventors generated a hybrid poliovirus which requires the activity of HCV protease NS3 for its proliferation, on the basis of the characteristics of HCV and poliovirus. The hybrid virus is composed of poliovirus and HCV. The proteins necessary for the proliferation and infection into other cells are produced by poliovirus gene for the hybrid virus. The poliovirus gene is preceded by HCV protease and the sites cleaved by the protease to construct this hybrid virus which requires HCV protease NS3 activity for viability. This virus is composed, sequentially, HCV NS3 protease domain plus its target site, and open reading frame of poliovirus which is necessary for virus replication and virus particle formation. The activity of the enzyme NS3 protease is necessary to survive the hybrid virus.

The hybrid virus is proliferable in the cultivation system to settle the conventional problem which HCV cannot be proliferated in vitro cultivation systems. Therefore, the hybrid virus enables to develop anti-HCV drugs based on protease inhibitor easily and precisely.

DETAILED DESCRIPTION OF THE DRAWINGS

The present invention will be described with reference to the accompanying drawings, in which:

FIG. 1 is schematic diagram of the genomic organization of poliovirus type 1 (Mahoney), NS3ΔC-PV1, and NS3ΔC-PV1.

Figure 2:
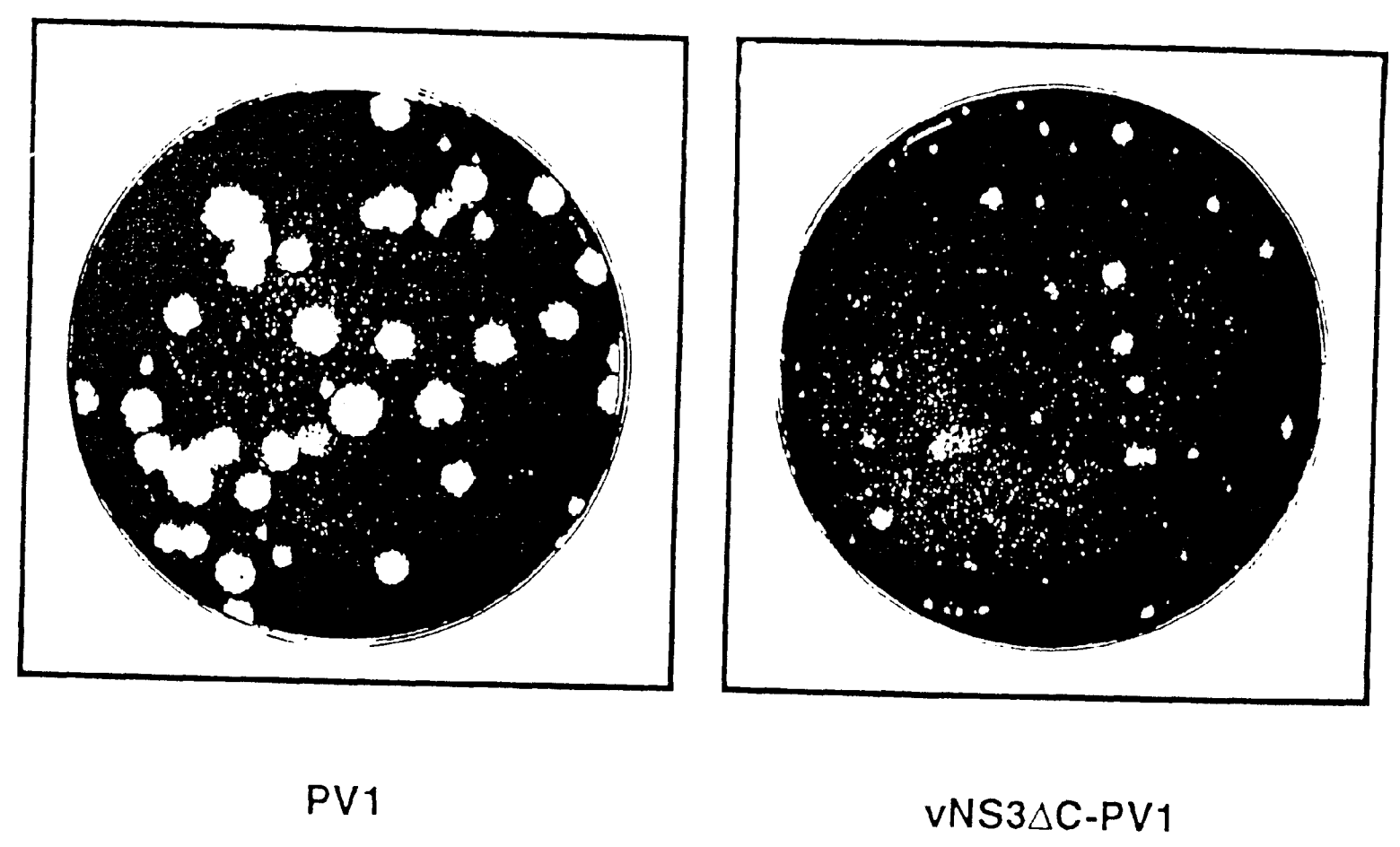

FIG. 2 is a photograph of plaque phenotypes of PV1 (M) and vNS3ΔC-PV1.

FIG. 3 is a photograph of RT-PCT analysis of vNS3ΔC-PV1 RNA.

Lane 1, 2 and 3 depict DNAs produced by PCR or RT-PCR using as template of pNS3ΔC-PV1, (+) sense RNA and (−) sense RNA, respectively.

FIGS. 4A, 4B and 4C are photographs of proteolytic processing patterns of PV1, NS3ΔC-PV1, and NS3ΔC-PV1 polyproteins.

FIG. 5 is one-step graph curves of PV1 (M) and vNS3ΔC-PV1. HeLa cells were infected with either PV1 or vNS3ΔC-PV1 at a multiplicity of infection of 10.

FIG. 6A to FIG. 6E (SEQ. ID. NOS. 10 to 14) present the genetic sequence of pNS3ΔC-PV1 according to an embodiment of the present invention.

DETAILED DESCRIPTION OF THE PREFERRED EMBODIMENTS

In the following detailed description, only the preferred embodiment of the invention has been shown and described, simply by way of illustration of the best mode contemplated by the inventor(s) of carrying out the invention, As will be realized, the invention is capable of modification in various obvious respects, all without departing from the invention, Accordingly, the drawing and description are to be regarded as illustrative in nature, and not as restrictive.

EXAMPLE

Material and Methods

Construction of Plasmids

DNA manipulations were carried out by standard methods (Sambrook et al., Molecular cloning: a laboratory manual (2nd ed.), Cold Spring Harbor Laboratory, Cold Spring Harbor, N.Y., 1989). The construction of the plasmids pTHEΔ1219–1634 and pPNENPO are described elsewhere (Han et al., *J. Gen. Virol.,* 76, 985–993, 1995; Alexander et al., *Proc. Natl. Acad. Sci.*, USA, 91, 1406–1410, 1994). pUC19 was cleaved with XbaI, treated with Klenow, and digested with PstI. The resulting 2.6 kb fragment was then ligated to the 1.3 kb fragment of pTHEΔ1219–1634 treated with NcoI, Klenow, and PstI in succession. The result was the construct pUC19-NS3ΔC-4ΔC. pPNENPO and pUC19-NS3 L C-4ΔC were digested with EcoRI or KpnI, respectively, and treated with Klenow enzyme. The linearized DNAs were ligated to result in the construct pPNENPO-NS3ΔA C-4ΔC.

To construct pNS3ΔC-4A-PV1, a polymerase chain reaction (PCR) was performed using the following four oligonucleotides:

Primer 1(SEQ ID NO: 1): 5'-TGATATCGAATTCCGG-3';

Primer 2(SEQ ID NO: 2): 5'-ATATGAGCTCCGCACTCTTCCATCTC-3';

Primer 3(SEQ ID NO: 3): 5'-ATATGAGCTCAGGTTTCATCACAGAAAG-3';

Primer 4(SEQ ID NO: 4): 5'-CTGTGCTAGCGCTTTTTG-3'.

The primers 1 plus 2 and pPNENPO-NS3ΔC-4ΔC were used to amplify the HCV protease NS3ΔC-4A region (PCR product 1). The PCR product 1 contains a new SacI site right after the NS4A-coding sequence. The primers 3 plus 4 and pPNENPO were used to amplify polioviral cDNA (746–2479) with a new SacI site at the beginning of the poliovirus ORF (PCR product 2). EcoRI and NheI digested pPNENPO, EcoRI and SacI digested PCR product 1, and SacI and NheI digested PCR product 2 were ligated together to generate plasmid pNS3ΔC-4A-PV1.

To construct pNS3ΔC-PV1, an oligonucleotide (5'-AGCTCCGCAGCAGACGACGTCCTCACTG-GCTTCCTCTTGCGOCGCCTCCTCCT CCGGTTGAGTTATCTGTGAAGAC-3') (SEQ ID NO: 5)encoding the C-terminal end of NS5A (P1-P10) and primer 1 were used to amplify the HCV region encoding amino acids 1016–1215. The PCR product was phosphorylated with polynucleotide kinase and then digested with EcoRI. pNS3ΔC-4A-PV1 was cleaved with SacI, treated with T4 DNA polymerase, and then digested with EcoRI. The larger fragment of pNS3ΔC-4A-PV1 was ligated to the PCR product to generate pNS3 ΔC-PV1. The junction sequences were confirmed by sequencing.

Site-directed mutagenesis of the serine in the catalytic triad of the HCV protease (Ser1165Ala).

Site-directed mutagenesis was carried out by the Kunkel method as previously described (Kunkel et al., Methods Enzymol., 154, 367, 1987). pSK1016–1650 was generated by ligation of the DNA fragments isolated from PvuII plus SalI-digested pTHE1016–1846 and SmaI plus SalI-digested pBluescript SK(+). E. coli strain RZ 1032 (ung$^-$dut$^-$) was transformed with pSK1016–1650, and ssDNA was prepared from the transformant. An oligonucleotide, 5'-CTTGAAGGGCTCCGCG GGTGG-3'(SEQ ID NO: 6), designed to change the serine residue in the catalytic triad of HCV protease to alanine [Ser 1165(TCG) to Ala(GCG)] was used for site directed mutagenesis. The oligonucleotide was phosphorylated with T4 polynucleotide kinase (Boehringer Mannheim) and annealed to the single stranded pSK1016–1650 DNA, extended with sequenase (USB), and ligated with T4 DNA ligase (Poscochem.) to result in covalently closed, circular, dsDNA. The ligated dsDNA was introduced into E. coli XL1-blue. The base change was confirmed by the presence of a newly generated SacII site and by sequencing. pSK1016–1650 (Ser1165Ala) was used to construct pNS3ΔC$^{--PV}$1 by replacing the XmaI fragment of pNS3ΔC-PV1 with the same fragment of pSK1016–1650 (Ser1165Ala).

In vitro Transcription and Translation Plasmid DNAs were purified following the polyethylene glycol precipitation method. They were then linearized with appropriate restriction enzymes downstream of the translation termination codon. The linearized DNAs were extracted with phenol/chloroform and ethanol-precipitated. RNAs were transcribed from the purified DNAs with T7 RNA polymerase (Boehringer Mannheim) as described by the manufacturer. These RNA transcripts were translated in a rabbit reticulocyte lysate system (RRL) supplemented with 25% HeLa cell lysate in the presence of [$^{35}$S] methionine. The in vitro translation reactions were carried out at 30° C. for 8 hours. The [$^{35}$S]-labeled proteins were analyzed on 15% SDS-PAGE using the buffer system described by Nicklin et al. (1987). The intensity of the autoradiographic images was enhanced by fluorography using salicylic acid. Gels were dried and exposed to Kodak XAR-5 film or Agfa Curix RP1 film.

RNA Transfection

An electroporation protocol was used to transfect HeLa cell monolayers with the viral RNAs prepared in vitro. Cells grown to 80% confluency were harvested. After two washes, the cells were resuspended in the medium at a concentration of 5×10$^6$ cells/ml. The cell suspension (1 ml) was mixed with 3 μg of RNA and placed in a 0.4 cm. Gene Pulser cuvette (BIO-RAD). The cuvette was electrically pulsed at 360 volt and 960 μl using the Gene Pulser transfection apparatus (BIO-RAD). Then the cells were diluted with 9 ml of medium containing 10% bovine calf serum, 5% equine serum, and 5% fetal calf serum.

Plaque Assay and One-step Growth Curve

Titers of virus stocks were measured by plaque assay on HeLa cell monolayers as follows. Cells were inoculated with virus, left for 30 minutes at room temperature, and then overlaid with Eagle medium containing 0.9% Noble agar and 5% fetal calf serum. Viral plaques were visualized with 0.5% crystal violet solution 60 hours postinfection.

Figure 5:
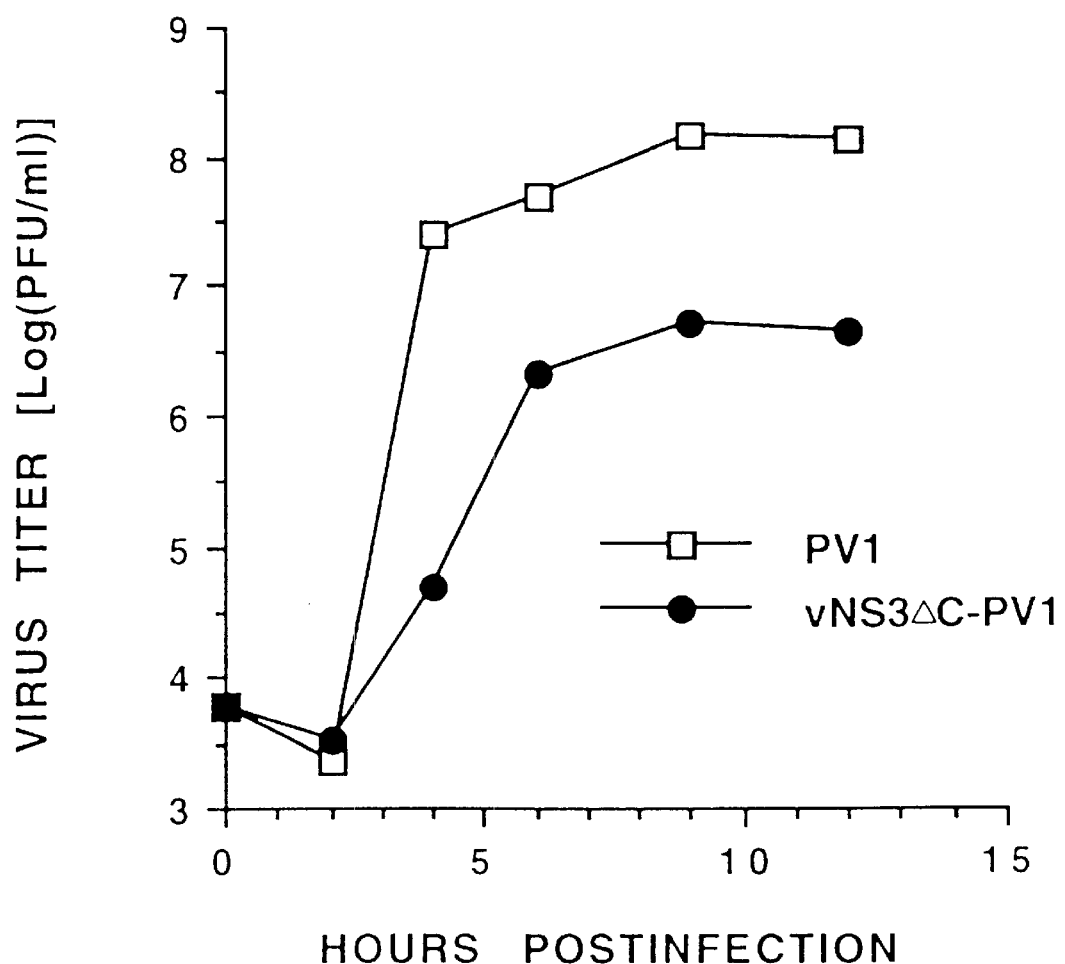

To measure one-step growth kinetics, virus was loaded onto 3.5 cm HeLa cell plates at a multiplicity of infection of 10 per cell and incubated at room temperature for 30 minutes to allow virus binding. Unbound particles were removed by two rounds of PBS washing. The infected cells were cultured at 37° C. in 2 ml of Eagle medium containing 10% bovine calf serum and harvested at the time points indicated in FIG. 5. The infectivity of the cell lysate at each time point was titrated by plaque assay.

Reverse Transcription PCR (RT-PCR)

Total RNA from virus-infected cells was isolated 4 hours postinfection as described by Lu et al. (1995). cDNAs were synthesized using M-MuLV reverse transcriptase and oligonucleotide primers corresponding to poliovirus nucleotides 556–570 and 789–806 (primer 5: 5'-GTGTTTCCTTTTATT-3'(SEQ ID NO: 7); primer 6: 5'-GTGTTTCCTTTTATT-3' (SEQ ID NO: 8). Primer 5 and primer 6 were used in synthesizing cDNAs from negative- and positive-sense RNA, respectively. Both of the primers were used in the PCR reaction that followed. The PCR products were analyzed on a 1.3 % agarose gel.

Labeling of Newly Synthesized Proteins in Virus-infected Cells

HeLa cells were infected with poliovirus 1 (Mahoney: PV1) and vNS3ΔC-PV1 at a multiplicity of infection of 30 PFU per cell. The cells were incubated in a medium lacking methionine for 10 minutes 3 hours after infection.

Subsequently, 100 μ Ci of [$^{35}$S] methionine was added to the medium and the incubation continued for 40 minutes. The cells were then collected and lysed. The lysate was analyzed on 15% SDS-PAGE.

Immunoblot Analysis

Virus-infected cells were lysed 4 hours postinfection. Total protein (13 μg) was resolved on a 15% SDS-PAGE gel and transferred onto a nitrocellulose membrane (Amersham). The blot was incubated overnight at 4° C. in blocking solution [20 mM Tris-HCl (pH 7.4), 150 mM NaCl, 0.5% Tween 20, and 5% powdered skim milk] to block nonspecific binding. The primary antibody (polyclonal antibody against HCV protease NS3) was added to the blocking solution for 3 hours. The antibody was a generous gift from Dr. R. Bartenschlager, Institute of Virology, Mainz, Germany. A horseradish peroxidase-linked anti-rabbit IgG in a 1:10,000 dilution was used as the secondary antibody. Membrane-bound antibodies were detected by enhanced chemiluminescence reagents (ECL; Amersham).

Generation of a Novel Poliovirus Containing HCV Protease NS3 and Its Target Site In order to develop an evaluation system for anti-HCV drugs targeting protease NS3, a recombinant poliovirus that requires the activity of HCV protease for its proliferation, was constructed. A schematic diagram of the genomic structure of this virus is depicted in FIG. 1. The hatched and open boxes represent HCV protease NS3ΔC and poliovirus polyprotein, respectively. The amino acid sequence at the junction of HCV protease NS3 and poliovirus P1 is indicated by single letter amino acid codes. The target site of HCV protease is marked by an arrowhead. The mutated amino acid (S1165A) in NS3ΔC$^{-PV}$1 is indicated by an asterisk.

As shown in FIG. 1, in the case of polyprotein NS3ΔC-PV1, the protease domain of HCV NS3 is fused to the last 10 amino acids of NS5A (EEASEDWCC(SEQ ID NO: 9)), which are recognized by protease NS3. These amino acids residues are preceded by four glycines, alanine, and glutamine serving as a hinge region between the protease domain and the target site. It was expected that the HCV protease NS3 would cleave the peptide bond between cysteine at the C-terminus of the additional polypeptide and glycine at the N-terminus of poliovirus P1, since HCV protease NS3 is known to cleave between the cysteine or threonine at the P1-residue and the small uncharged residues at the P1'-residue (Kolykhalov et al., J. Virol. 68, 7525–7533, 1994; Komoda et al., J. Virol., 68, 7351-7357, 1994).

Upon transfection, the RNA transcript encoding NS3ΔC-PV1 produced a virus designated vNS3ΔC-PV1. On the other hand, the RNA transcript similar to NS3ΔC-PV1 but containing a serine to alanine mutation at the catalytic triad of HCV protease NS3 (NS3ΔC$^{--PV}$1) did not yield virus. This strongly suggests that HCV protease NS3 activity is essential for the viability of the hybrid virus vNS3ΔC-PV1. The virus vNS3ΔC-PV1 has a small plaque phenotype at 37° C. as shown in FIG. 2. (compare plaque sizes in panel PV1 with vNS3ΔC-PV1) or at 30° C. (data not shown).

The virus vNS3ΔC-PV1 is stable through at least five passages. The integrity of vNS3ΔC-PV1 was confirmed by analyzing the viral RNAs in cells inoculated with a virus stock of the fourth passage. Lanes 1, 2 and 3 depict DNAs produced by PCR or RT-PCR using as templates plasmid pNS3ΔC-PV1, (+) sense RNA, respectively. The inserted HCV sequence in the poliovirus genome was amplified by RT-PCT with primers annealing to the poliovirus 5'nontranslated region and the P1-coding region. The viral RNAs of the fifth passage retained the inserted HCV protease and NS5A sequences as shown in FIG. 3. Both positive and negative sense viral RNAs of the expected sizes were detected (FIG. 3, lanes 2 and 3, respectively). RT-PCR analysis of the genomic RNAs isolated from vNS3ΔC-PV1 virion particles revealed the same RT-PCR products as the RNAs isolated from HeLa cells (data not shown). The junction sequence between HCV and poliovirus was confirmed by DNA-sequencing of the PCR products and the sequences of hepatitis C surrogate virus genome is presented in FIG. 6. This indicates that vNS3ΔC-PV1 is stable at least for five passages.

Proper Proteolytic Processing of vNS3ΔC-PV1 Polyprotein Requires HCV NS3 Protease Activity.

Proteolytic processing patterns of polyproteins encoded by poliovirus, vNS3ΔA C-PV1, and NS3ΔC$^-$-PV1 RNA were analyzed by in vitro transcription and translation of pT7-PC1, pNS3ΔC-PV1, and pNS3ΔC$^-$-PV1. Most of the polioviral proteins were detected as in vitro translation products of the PV1 RNA transcript (FIG. 4A, lane 1). Two additional protein bands of 123 kDa and 26 kDa were apparent among the translation products of NS3ΔC-PV1 as compared to the PV1-translation product (FIG. 4A, lane 2). The 123 kDa and 26 kDa proteins are most likely NS3ΔC-P1 fusion protein and the processed NS3ΔC, respectively, since the cleavage of poliovirus at the P1/P2 junction occurs very fast, even during the process of translation. Translation of vNS3ΔC$^-$-PV1 also yielded the 123 kDa protein. But the 26 kDa and the P1 protein were not detected among the translation products from this construct (FIG. 4A, lane 3). This indicates that proteolytic cleavage of the HCV/poliovirus junction does not occur in NS3ΔC$^-$-PV1, and that the cleavage of this junction is mediated by the protease activity of NS3. It also shows that the failure of virus production with the NS3 ΔC$^-$-PV1 construct is most likely due to the lack of the P1 polypeptide which is a protein processed into viral coat protein (VP0, VP1, and VP3). In other words, HCV NS3 activity is essential for proliferation of the vNS3 ΔC-PV1. Interestingly, complete processing of the viral capsid proteins (VP0, VP1, and VP3) from the NS3 ΔC$^-$-PV1 polyprotein was not detected. On the other hand, the processed capsid proteins were apparent along with the precursor NS3ΔC-P1 (compare lane 2 with lane 3 in FIG. 4A). The blockage of proteolytic processing of the NS3ΔC$^-$-PV1 polyprotein may be due to the lack of myristoylation of the glycine residue at the N-terminus of P1 that has been shown to be important in the processing of P1 by poliovirus protease 3C-3D (Krausslich et al., *J. Virol.,* 64, 2433–2436, 1990).

The proteolytic processing was also investigated for PV1 and vNS3ΔC-P1 by labeling newly synthesized proteins with [$^{35}$S] methionine in virus-infected cells. The labeling in vNS3ΔC-PV1-infected cells showed four additional bands with apparent molecular weights of 123 kDa, 89 kDa, 63 kDa and 26 kDa as indicated by arrow heads (FIG. 4B, compare lane 2 with lane 3). These proteins are most likely NS3ΔC-P1, NS3ΔC-VP0-VP3, NS3 L C-VP0, and NS3ΔC, respectively (FIG. 4B). This assumption is supported by the Western blotting analysis using an antibody against HCV NS3 and HeLa cell extracts after infection with either wild type poliovirus or vNS3ΔC-PV1 (FIG. 4C). Among the proteins of vNS3ΔC-PV1-infected cells, the anti-NS3 antibody recognized the 63 kDa and the 26 kDa polypeptides corresponding to vNS3ΔC-VP0 and NS3ΔC, respectively (FIG. 4C, lane 3). A longer exposure of the X-ray film also revealed the 123 kDa band and the 89 kDa band corresponding to NS3ΔC-P1 and NS3 ΔC-VP0-VP3, respectively (data not shown). On the other hand, no bands were detected in the Western analysis of cell extracts from wild type poliovirus- or mock-infected cells (FIG. 4C, lanes 1 and 2). The results indicate that proteolytic processing of the artificial polyprotein occurs as expected, even though the HCV/poliovirus junction cleavage happens slower than the P1/P2 junction cleavage. The relative intensities of the NS3-related bands varied depending on the methodologies used to detect the polypeptides. For instance, a strong band of NS3ΔC-P1 was detected by in vitro and in vivo labeling, but only a weak band of NS3ΔC-P1 was detected by Western blot analysis. The [$^{35}$S] methionine labeling method reveals only newly synthesized polypeptides and larger proteins, containing more methionine residues, give stronger signals. Western blot analysis, on the other hand, reveals all of the proteins interacting with the primary antibody, and the intensity of the signal reflects the molarities of the proteins rather than their size. Therefore, [$^{35}$S] methionine labeling methods are expected to give relatively stronger signals for precursor forms than Western blot analysis methods.

One-step growth kinetics of chimeric virus vNS3ΔC-PV1

FIG. 5 was one step growth curve for vNS3ΔC-PV1. While maximum production of wild type poliovirus was reached 4 hours postinfection (FIG. 5, open squares), that of vNS3ΔC-PV1 was delayed by about 2 hours (FIG. 5, closed circles). In FIG. 5, the titer of vNS3ΔC-PV1 at the peak was about 1'.5 orders of magnitude lower than that of wild type poliovirus, as viral titers at 9 hours postinfection was compared. The small plaque phenotype of vNS3ΔC-PV1 may thus be a result of delayed virion particle formation and smaller burst size.

The HCV protease NS3 activity is necessary for noble poliovirus according to the present invention to survive. This virus is useful for testing the efficacy of anti-virus drugs which targets protease NS3.

What is claimed is:

1. A construct encoding a recombinant virus, said construct comprising a first nucleic acid encoding hepatitis C virus protease NS3, a second nucleic acid encoding a target site for said NS3, and a third nucleic acid encoding poliovirus.

2. The construct of claim 1, wherein said target site is selected from the group consisting of NS5A/5B, NS4A/4B and NS4B/5A.

3. The construct of claim 1 wherein said target site is NS5A/5B and said NS5A/5B has a C-terminal cysteine, and wherein said poliovirus has an N-terminal glycine.

4. A screening method for anti-hepatitis C virus drugs comprising the steps of:

(a) proliferating a virus encoded by the construct of claim 1 in the presence of a material to be screened;

(b) proliferating said virus in the absence of said material; and (c) comparing proliferation in the presence and absence of said material, wherein decreased proliferation in the presence of said material as compared to proliferation in the absence of said material is indicative of a positive screening result.

5. A method of measuring the activity of an anti-hepatitis C virus drug comprising the steps of:

(a) proliferating a virus encoded by the construct of claim 1 in the presence of an anti-hepatitis C virus drug;

(b) proliferating said virus in the absence of said drug; and (c) measuring proliferation in the presence and absence of said drug, wherein the decrease in proliferation in the presence of said drug is correlated with the activity of said drug.

6. A recombinant virus encoded by the construct of claim 1.

* * * * *

UNITED STATES PATENT AND TRADEMARK OFFICE
CERTIFICATE OF CORRECTION

PATENT NO. : 6,395,471 B1
DATED : May 28, 2002
INVENTOR(S) : Jang et al.

It is certified that error appears in the above-identified patent and that said Letters Patent is hereby corrected as shown below:

Column 3,
Line 6, "5'-nontraslated" should read -- 5'-nontranslated --
Line 8, "Pelletiet" should read -- Pelletier --

Column 4,
Line 29, "L" should read -- $\Delta$ --
Line 59, "5)encoding" should read -- 5) encoding --

Column 5,
Line 23, "pNS3$\Delta$C$^{-PV}$1" should read -- pNS3$\Delta$C$^{\bullet}$-PV1 --

Column 6,
Line 52, "NS3$\Delta$C$^{-PV}$1" should read -- NS3$\Delta$C-PV1 --
Line 55, "(EEASEDWCC(SEQ ID NO: 9))," should read -- (EEASEDVVCC)(SEQ ID NO: 9), --

Column 7,
Line 5, "(NS3$\Delta$C$^{-PV}$1)" should read -- (NS3$\Delta$C$^{\bullet}$-PV1) --
Line 38, "NS3$\Delta$C$^-$-PV1" should read -- NS3$\Delta$C$^{\bullet}$-PV1) --
Line 40, "pNS3$\Delta$C$^-$-PV1." should read -- pNS3$\Delta$C$^{\bullet}$-PV1. --
Line 51, "vNS3$\Delta$C$^-$-PV1" should read -- vNS3$\Delta$C$^{\bullet}$-PV1 --
Line 55, "NS3$\Delta$C$^-$-PV1," should read -- NS3$\Delta$C$^{\bullet}$-PV1, --
Line 59, "NS3$\Delta$C$^-$-PV1" should read -- NS3$\Delta$C$^{\bullet}$-PV1 --
Line 65, "$\Delta$C$^-$-PV1" should read -- $\Delta$C$^{\bullet}$-PV1 --

Column 8,
Line 2, "NS3$\Delta$C$^-$-" should read -- NS3$\Delta$C$^{\bullet}$- --
Line 17, "L" should read -- $\Delta$ --
Line 25, "vNS3$\Delta$C-VP0" should read -- vNS3$\Delta$C-VP0 --
Line 67, "targets" should read -- target --

UNITED STATES PATENT AND TRADEMARK OFFICE
CERTIFICATE OF CORRECTION

PATENT NO. : 6,395,471 B1
DATED : May 28, 2002
INVENTOR(S) : Jang et al.

It is certified that error appears in the above-identified patent and that said Letters Patent is hereby corrected as shown below:

Column 23,
Line 1, "comprising a first" should read -- comprising: ¶a first --

Signed and Sealed this

First Day of July, 2003

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 1
tgatatcgaa ttccgg                                                   16

<210> SEQ ID NO 2
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 2
atatgagctc cgcactcttc catctc                                        26

<210> SEQ ID NO 3
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 3
atatgagctc aggtttcatc acagaaag                                      28

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 4
ctgtgctagc gcttttg                                                  18

<210> SEQ ID NO 5
<211> LENGTH: 75
<212> TYPE: DNA
<213> ORGANISM: Artificial Sequence
<220> FEATURE:
<223> OTHER INFORMATION: Oligonucleotide Primer ba sed in part on the
      sequnce encoding the carboxy-terminal end of NS5A

<400> SEQUENCE: 5
agctccgcag cagacgacgt cctcactggc ttcctcttgc gcgcctcctc c tccggttga   60 gttatctgtg aagac                                                    75

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 6
cttgaagggc tccgcgggtg g                                             21

```
<210> SEQ ID NO 7
<211> LENGTH: 15
<212> TYPE: DNA
<213> ORGANISM: Poliovirus
<220> FEATURE:
<221> NAME/KEY: misc_feature
<222> LOCATION: (1)...(15)
<223> OTHER INFORMATION: Oligonucleotide primer co rresponding to
      poliovirus nucleotides 556-570

<400> SEQUENCE: 7
gtgtttcctt ttatt                                                    15

<210> SEQ ID NO 8
<211> LENGTH: 18
<212> TYPE: DNA
<213> ORGANISM: Poliovirus
<220> FEATURE:
<221> NAME/KEY: misc_feature
<222> LOCATION: (1)...(18)
<223> OTHER INFORMATION: Oligonucleotide primer co rresponding to
      poliovirus nucleotides 789-806

<400> SEQUENCE: 8
caccatacgc tctatttg                                                 18

<210> SEQ ID NO 9
<211> LENGTH: 10
<212> TYPE: PRT
<213> ORGANISM: Hepatitis C Virus
<220> FEATURE:
<221> NAME/KEY: PEPTIDE
<222> LOCATION: (1)...(10)
<223> OTHER INFORMATION: Carboxy-terminal residues of NS5A

<400> SEQUENCE: 9

Glu Glu Ala Ser Glu Asp Val Val Cys Cys
 1               5                  10

<210> SEQ ID NO 10
<211> LENGTH: 2320
<212> TYPE: DNA
<213> ORGANISM: Artificial Sequence
<220> FEATURE:
<223> OTHER INFORMATION: Genetically engineered vi rus derived from
      poliovirus and hepatitis C virus

<400> SEQUENCE: 10
ttaaaacagc tctggggttg tacccacccc agaggcccac gtggcggcta g tactccggt    60 attgcggtac ccttgtacgc ctgtttttata ctcccttccc gtaacttaga c gcacaaaac   120 caagttcaat agaagggggt acaaaccagt accaccacga caagcacttt c tgtttcccc   180 ggtgatgtcg tatagactgc ttgcgtggtt gaaagcgacg gatccgttat c cgcttatgt   240 acttcgagaa gcccagtacc acctcggaat cttcgatgcg ttgcgctcag c actcaaccc   300 cagagtgtag cttaggctga tgagtctgga catccctcac cggtgacggt g gtccaggct   360 gcgttggcgg cctacctatg gctaacgcca tgggacgcta gttgtgaaca a ggtgtgaag   420 agcctattga gctacataag aatcctccgg ccccctgaatg cggctaatcc c aacctcgga   480 gcaggtggtc acaaaccagt gattggcctg tcgtaacgcg caagtccgtg g cggaaccga   540 ctactttggg tgtccgtgtt tcctttttatt ttattgtggc tgcttatggt g acaatcaca   600 gattgttatc ataaagcgaa gacggtatag cttgatatcg aattccgggg a tcctctagc   660 atggccagtc atcatcatca tcatcatgga attgtcgaca attccccggc c gatagcctt   720
```

-continued

```
gaagggcagg ggtggcaact ccccgctccc atcacggcct actcccaaca g acgcggggc    780 ctacttggtt gcatcatcac tagcctcaca ggccgggaca agaaccaagt c gaggggggag   840 gttcaagtgg tttccaccgc aacacaatct ttcctggcga cctgcgtcaa t ggcgcttgg    900 actgtcttcc atggtgccgg ctcaaagacc ctagccggcc caaagggcca a ttacccaaa    960 tgtacaccaa tgtagacctg gacctcgtcg gctggcaggc accccccggg t cgcgtcccc   1020 tgacaccatg cacctgcggc agctcagacc tttacttggt cacgagacat g ctgatgtca   1080 ttccggtgcg ccggcgggc gacagtaggg ggagcctacc ctctcccaga c cagtctcct    1140 acttgaaggg ctcctcgggt ggtccactgc tctgcccttc ggggcacgct g ttggcatct   1200 ttcgggctgc tgtatgcacc cggggggttg cgaaggcggt ggacttcata c ccgttgaat   1260 ctatggaaac tactatgcgg tctccggtct tcacagataa ctcaaccgga g gaggaggcg   1320 cgcaagagga agccagtgag gacgtcgtct gctgcgagc tcaggtttca t cacagaaag    1380 tgggcgcaca tgaaaactca aatagagcgt atggtggttc taccattaaa t tacaccacc   1440 attaattatt atagagattc agctagtaac gcggcttcga aacaggactt c tctcaagac   1500 ccttccaagt tcaccgagcc catcaaggat gtcctgataa aaacagcccc a atgctaaac   1560 tcgccaaaca tagaggcttg cgggtatagc gatagagtac tgcaattaac a ctgggaaac   1620 tccactataa ccacacagga ggcggctaat tcagtagtcg cttatgggcg t tggcctgaa   1680 tatctgaggg acagcgaagc caatccagtg gaccagccga cagaaccaga c gtcgctgca   1740 tgcaggtttt atacgctaga caccgtgtct tggacgaaag agtcgcgagg g tggtggtgg   1800 aagttgcctg atgcactgag ggacatggga ctctttgggc aaaatatgta c taccactac   1860 ctaggtaggt ccgggtacac cgtgcatgta cagtgtaacg cctccaaatt c caccagggg   1920 gcactagggg tattcgccgt accagagatg tgtctggccg gggatagcaa c accactacc   1980 atgcacacca gctatcaaaa tgccaatcct ggcgagaaag gaggcacttt c acgggtacg   2040 ttcactcctg acaacaacca gacatcacct gcccgcaggt tctgcccggt g gattacctc   2100 cttggaaatg gcacgttgtt ggggaatgcc tttgtgttcc cgcaccagat a ataaaccta   2160 cggaccaaca actgtgctac actggtactc ccttacgtga actccctctc g atagatagt   2220 atggtaaagc acaataattg gggaattgca atattaccat tggcccccatt a aattttgct   2280 agtgagtcct ccccagagat tccaatcacc ttgaccatag                          2320
```

<210> SEQ ID NO 11
<211> LENGTH: 2321
<212> TYPE: DNA
<213> ORGANISM: Artificial Sequence
<220> FEATURE:
<223> OTHER INFORMATION: Genetically engineered vi rus derived from poliovirus and hepatitis C virus

<400> SEQUENCE: 11

```
cccctatgtg ctgtgagttc aatggattaa gaaacatcac cctgccacgc t tacagggcc     60
tgccggtcat gaacacccct ggtagcaatc aatatcttac tgcagacaac t tccagtcac    120
cgtgtgcgct gcctgaattt gatgtgaccc cacctattga catacccggt g aagtaaaga    180
acatgatgga attggcagaa atcgacacca tgattccctt tgacttaagt g ccacaaaaa    240
agaacaccat ggaaatgtat agggttcggt taagtgacaa accacataca g acgatccca    300
tactctgcct gtcactctct ccagcttcag atcctaggtt gtcacatact a tgcttggag    360
aaatcctaaa ttactacaca cactgggcag gatccctgaa gttcacgttt c tgttctgtg    420
```

```
gatccatgat ggcaactggc aaactgttgg tgtcatacgc gcctcctgga g ccgacccac      480 caaagaagcg taaggaggcg atgttgggaa cacatgtgat ctgggacata g gactgcagt      540 cctcatgtac tatggtagtg ccatggatta gcaacaccac gtatcggcaa a ccatagatg      600 atagtttcac cgaaggcgga tacatcagcg tcttctacca aactagaata g tcgtccctc      660 tttcgacacc cagagagatg gacatccttg gttttgtgtc agcgtgtaat g acttcagcg      720 tgcgcttgtt gcgagatacc acacatatag agcaaaaagc gctagcacag g ggttaggtc      780 agatgcttga aagcatgatt gacaacacag tccgtgaaac ggtgggggcg g caacatcta      840 gagacgctct cccaaacact gaagccagtg gaccaacaca ctccaaggaa a ttccggcac      900 tcaccgcagt ggaaactggg gccacaaatc cactagtccc ttctgataca g tgcaaacca      960 gacatgttgt acaacatagg tcaaggtcag agtctagcat agagtctttc t tcgcgcggg     1020 gtgcatgcgt gaccattatg accgtggata acccagcttc caccacgaat a aggataagc     1080 ttttttgcagt gtggaagatc acttataaag atactgtcca gttacggagg a aattggagt     1140 tcttcaccta ttctagattt gatatggaac ttaccttttgt ggttactgca a atttcactg     1200 agactaacaa tggccatgca ttaaatcaag tgtaccaaat tatgtacgta c caccaggcg     1260 ctccagtgcc cgaaaaatgg gacgactaca catggcaaac ctcatcaaat c catcaatct     1320 tttacaccta cgggacagct ccagcccgga tctcggtacc gtatgttggt a tttcgaacg     1380 cctattcaca cttttacgac ggttttttcca aagtaccact gaaggaccag t cggcagcac     1440 taggtgactc cctttatggt gcagcatctc taaatgactt cggtatttttg g ctgttagag     1500 tagtcaatga tcacaacccg accaaggtca cctccaaaat cagagtgtat c taaaaccca     1560 aacacatcag agtctggtgc cgcgtccac cgagggcagt ggcgtactac g gccctggag     1620 tggattacaa ggatggtacg cttacacccc tctccaccaa ggatctgacc a catatggat     1680 tcggacacca aaacaaagcg gtgtacactg caggttacaa aatttgcaac t accacttgg     1740 ccactcagga tgatttgcaa aacgcagtga acgtcatgtg gaagtagaga c ctcttagtc     1800 acagaatcaa gagcccaggg caccgattca atcgcaaggt gcaattgcaa c gcaggggtg     1860 tactactgcg agtctagaag gaaatactac ccagtatcct tcgttggccc a acgttccag     1920 tacatggagg ctaataacta ttacccagct aggtaccagt cccatatgct c attggccat     1980 ggattcgcat ctccagggga ttgtggtggc atactcagat gtcaccacgg g gtgataggg     2040 atcattactg ctggtggaga agggttggtt gcattttcag acattagaga c ttgtatgcc     2100 tacgaagaag aagccatgga acaaggcctc accaattaca tagagtcact t ggggccgca     2160 tttggaagtg gatttactca gcagattagc gacaaaataa cagagttgac c aatatggtg     2220 accagtacca tcactgaaaa gctacttaag aacttgatca agatcatatc c tcactagtt     2280 attataacta ggaactatga agacaccaca acagtgctcg c                        2321
```

<210> SEQ ID NO 12
<211> LENGTH: 2319
<212> TYPE: DNA
<213> ORGANISM: Artificial Sequence
<220> FEATURE:
<223> OTHER INFORMATION: Genetically engineered vi rus derived from
      poliovirus and hepatitis C virus

<400> SEQUENCE: 12

```
taccctggcc cttcttgggt gtgatgcttc accatggcag tggcttagaa a gaaagcatg       60 cgatgttctg gagatacctt atgtcatcaa gcaaggtgac agttggttga a gaagtttac      120
```

-continued

```
tgaagcatgc aacgcagcta agggcctgga gtgggtgtca acaaaatct c aaaattcat    180 tgattggctc aaggagaaaa ttatcccaca agctagagat aagttggaat t tgtaacaaa   240 acttagacaa ctagaaatgc tggaaaacca aatctcaact atacaccaat c atgccctag   300 tcaggaacac caggaaattc tattcaataa tgtcagatgg ttatccatcc a gtctaagag   360 gtttgcccct ctttacgcag tggaagccaa agaatacgaa aaactcgagc a tactattaa   420 caactacata cagttcaaga gcaaacaccg tattgaacca gtatgtttgc t agtacatgg   480 cagccccgga acaggtaaat ctgtagcaac caacctgatt gctagagcca t agctgaaag   540 agaaaacacg tccacgtact cgctaccccc ggatccatca cacttcgacg g atacaaaca   600 acagggagtg gtgattatgg acgacctgaa tcaaaaccca gatggtgcgg a catgaagct   660 gttctgtcag atggtatcaa cagtggagtt tataccaccc atggcatccc t ggaggagaa   720 aggaatcctg tttacttcaa attacgttct agcatccaca aactcaagca g aatttcccc   780 ccccactgtg gcacacagtg acgcgttagc caggcgcttt gcgttcgaca t ggacattca   840 ggtcatgaat gagtattcta gagatgggaa attgaacatg ccatggcta c tgaaatgtg    900 taagaactgt caccaaccag caaactttaa gagatgctgt cctttagtgt g tggtaaggc   960 aattcaatta atggacaaat cttccagagt tagatacagt attgaccaga t cactacaat  1020 gattatcaat gagagaaaca gaagatccaa cattggcaat tgtatggagg c tttgtttca  1080 aggaccactc cagtataaag acttgaaatt gacatcaaga cgagtccccc t cctgaatgt  1140 atcaatgact tgctccaagc agttgactcc caggaggtga gagattactg t gagaagaag  1200 ggttggatag ttaacatcac cagccaggtt caaacagaaa ggaacatcaa c aggcaatg   1260 acaattctac aagcggtgac aaccttcgcc gcagtggctg gagttgtcta t gtcatgtat  1320 aaactgtttg ctggacacca gggagcatac actggtttac caaacaaaaa a cccaacgtg  1380 cccaccattc ggacagcaaa ggtacaagga ccagggttcg attacgcagt g gctatggct  1440 aaaagaaaca ttgttacagc aactactagc aaggagagt tcactatgtt a ggagtccac   1500 gacaacgtgg ctattttacc aacccacgct tcacctggtg aaagcattgt g atcgatggc  1560 aaagaagtgg agatcttgga tgccaaagcg ctcgaagatc aagcaggaac c aatcttgaa  1620 atcactataa tcactctaaa gagaaatgaa aagttcagag acattagacc a catatacct  1680 actcaaatca ctgagacaaa tgatggagtc ttgatcgtga acactagcaa g taccccaat  1740 atgtatgttc ctgtcggtgc tgtgactgaa cagggatatc taaatctcgg t gggcgccaa  1800 actgctcgta ctctaatgta caactttcca accagagcag gacagtgtgg t ggagtcatc  1860 acatgtactg ggaaagtcat cgggatgcat gttggtggga cggttcaca c gggtttgca   1920 gcggccctga gcgatcata cttcactcag agtcaaggtg aaatccagtg g atgagacct  1980 tcgaaggaag tgggatatcc aatcataaat gccccgtcca aaaccaagct t gaacccagt  2040 gctttccact atgtgtttga agggtgaag gaaccagcag tcctcactaa a aacgatccc   2100 aggcttaaga cagactttga ggaggcaatt ttctccaagt acgtgggtaa c aaaattact  2160 gaagtggatg agtacatgaa agaggcagta gaccactatg ctggccagct c atgtcacta  2220 gacatcaaca cagaacaaat gtgcttggag gatgccatgt atggcactga t ggtctagaa  2280 gcacttgatt tgtccaccag tgctggctac ccttatgta                          2319
```

<210> SEQ ID NO 13
<211> LENGTH: 2320
<212> TYPE: DNA

<213> ORGANISM: Artificial Sequence
<220> FEATURE:
<223> OTHER INFORMATION: Genetically engineered vi rus derived from
       poliovirus and hepatitis C virus

<400> SEQUENCE: 13

| | | | | | |
|---|---|---|---|---|---|
| gcaatgggaa | agaagaagag | agacatcttg | aacaaacaaa | ccagagacac t | aaggaaatg | 60 |
| caaaaactgc | tcgacacata | tggaatcaac | ctcccactgg | tgacttatgt a | aaggatgaa | 120 |
| cttagatcca | aaacaaaggt | tgagcagggg | aaatccagat | taattgaagc t | tctagtttg | 180 |
| aatgactcag | tggcaatgag | aatggctttt | gggaacctat | atgctgcttt t | cacaaaaac | 240 |
| ccaggagtga | taacaggttc | agcagtgggg | tgcgatccag | atttgttttg g | agcaaaatt | 300 |
| ccggtattga | tggaagagaa | gctgtttgct | tttgactaca | cagggtatga t | gcatctctc | 360 |
| agccctgctt | ggttcgaggc | actaaagatg | gtgcttgaga | aaatcggatt c | ggagacaga | 420 |
| gttgactaca | tcgactacct | aaaccactca | caccacctgt | acaagaataa a | acatactgt | 480 |
| gtcaagggcg | gtatgccatc | tggctgctca | ggcacttcaa | tttttaactc a | atgattaac | 540 |
| aacttgatta | tcaggacact | cttactgaaa | acctacaagg | gcatagattt a | gaccaccta | 600 |
| aaaatgattg | cctatggtga | tgatgtaatt | gcttcctacc | cccatgaagt t | gacgctagt | 660 |
| ctcctagccc | aatcaggaaa | agactatgga | ctaactatga | ctccagctga c | aaatcagct | 720 |
| acatttgaaa | cagtcacatg | ggagaatgta | acattcttga | agagattctt c | agggcagac | 780 |
| gagaaatacc | catttcttat | tcatccagta | atgccaatga | aggaaattca t | gaatcaatt | 840 |
| agatggacta | agatcctag | gaacactcag | gatcacgttc | gctctctgtg c | cttttagct | 900 |
| tggcacaatg | gcgaagaaga | atataacaaa | ttcctagcta | aaatcaggag t | gtgccaatt | 960 |
| ggaagagctt | tattgctccc | agagtactca | acattgtacc | gccgttggct t | gactcattt | 1020 |
| tagtaaccct | acctcagtcg | aattggattg | ggtcatactg | ttgtagggt a | aattttct | 1080 |
| ttaattcgga | ggaaaaaaaa | aaaaaaaaaa | aaaaaaaaaa | aaaaaaaaaa a | aaaaaaaaa | 1140 |
| aaaaaaaaaa | aaaaaaaaaa | aaaaaaaaaa | aaacggaatt | aattcttgaa g | acgaaaggg | 1200 |
| cctcgtgata | cgcctatttt | tataggttaa | tgtcatgata | ataatggttt c | ttagacgtc | 1260 |
| aggtggcact | tttcggggaa | atgtgcgcgg | aaccccctatt | tgtttatttt t | ctaaataca | 1320 |
| ttcaaatatg | tatccgctca | tgagacaata | accctgataa | atgcttcaat a | atattgaaa | 1380 |
| aaggaagagt | atgagtattc | aacatttccg | tgtcgccctt | attccctttt t | tgcggcatt | 1440 |
| ttgccttcct | gtttttgctc | acccagaaac | gctggtgaaa | gtaaaagatg c | tgaagatca | 1500 |
| gttgggtgca | cgagtgggtt | acatcgaact | ggatctcaac | agcggtaaga t | ccttgagag | 1560 |
| ttttcgcccc | gaagaacgtt | ttccaatgat | gagcactttt | aaagttctgc t | atgtggcgc | 1620 |
| ggtattatcc | cgtgttgacg | ccgggcaaga | gcaactcggt | cgccgcatac a | ctattctca | 1680 |
| gaatgacttg | gttgagtact | caccagtcac | agaaaagcat | cttacggatg g | catgacagt | 1740 |
| aagagaatta | tgcagtgctg | ccataaccat | gagtgataac | actgcggcca a | cttacttct | 1800 |
| gacaacgatc | ggaggaccga | aggagctaac | cgcttttttg | cacaacatgg g | ggatcatgt | 1860 |
| aactcgcctt | gatcgttggg | aaccggagct | gaatgaagcc | ataccaaacg a | cgagcgtga | 1920 |
| caccacgatg | cctgcagcaa | tggcaacaac | gttgcgcaaa | ctattaactg g | cgaactact | 1980 |
| tactctagct | tcccggcaac | aattaataga | ctggatggag | gcggataaag t | tgcaggacc | 2040 |
| acttctgcgc | tcggcccttc | cggctggctg | gtttattgct | gataaatctg g | agccgtga | 2100 |
| gcgtgggtct | cgcggtatca | ttgcagcact | ggggccagat | ggtaagccct c | ccgtatcgt | 2160 |

-continued

| | |
|---|---|
| agttatctac acgacgggga gtcaggcaac tatggatgaa cgaaatagac a gatcgctga | 2220 |
| gataggtgcc tcactgatta agcattggta actgtcagac caagtttact c atatatact | 2280 |
| ttagattgat ttaaaacttc atttttaatt taaaaggatc | 2320 |

<210> SEQ ID NO 14
<211> LENGTH: 2047
<212> TYPE: DNA
<213> ORGANISM: Artificial Sequence
<220> FEATURE:
<223> OTHER INFORMATION: Genetically engineered vi rus derived from
      poliovirus and hepatitis C virus

<400> SEQUENCE: 14

| | |
|---|---|
| taggtgaaga tcctttttga taatctcatg accaaaatcc cttaacgtga g ttttcgttc | 60 |
| cactgagcgt cagaccccgt agaaagatc aaaggatctt cttgagatcc t tttttctg | 120 |
| cgcgtaatct gctgcttgca acaaaaaaa ccaccgctac cagctggttt g tttgccgga | 180 |
| tcaagagcta ccaactcttt ttccgaaggt aactggcttc agcagagcgc a gataccaaa | 240 |
| tactgtcctt ctagtgtagc cgtagttagg ccaccacttc aagaactctg t agcaccgcc | 300 |
| tacataccte gctctgctaa tcctgttacc agtggctgct gccagtggcg a taagtcgtg | 360 |
| tcttaccggg ttggactcaa gacgatagtt accggataag gcgcagcggt c gggctgaac | 420 |
| ggggggttcg tgcacacagc ccagcttgga gcgaacgacc tacaccgaac t gagatacct | 480 |
| acagcgtgag cattgagaaa gcgccacgct cccgaagggg agaaaggcgg a caggtatcc | 540 |
| ggtaagcggc agggtcggaa caggagagcg cacgagggag cttccagggg g aaacgcctg | 600 |
| gtatctttat agtcctgtcg ggtttcgcca cctctgactt gagcgtcgat t tttgtgatg | 660 |
| ctcgtcaggg gggcggagcc tatggaaaaa cgccagcaac gcggccttt t acggttcct | 720 |
| ggccttttgc tggccttttg ctcacatgtt ctttcctgcg ttatcccctg a ttctgtgga | 780 |
| taaccgtatt accgcctttg agtgagctga taccgctcgc cgcagccgaa c gaccgagcg | 840 |
| cagcgagtca gtgagcgagg aagcggaaga gcgcctgatg cggtattttc t ccttacgca | 900 |
| tctgtgcggt atttcacacc gcatatggtg cactctcagt acaatctgct c tgatgccgc | 960 |
| atagttaagc cagtatacac tccgctatcg ctacgtgact gggtcatggc t gcccccga | 1020 |
| cacccgccaa cacccgctga cgcgccctga cgggcttgtc tgctcccggc a tccgcttac | 1080 |
| agacaagctg tgaccgtctc cgggagctgc atgtgtcaga ggttttcacc g tcatcaccg | 1140 |
| aaacgcgcga ggcagctgcg gtaaagctca tcagcgtggt cgtgaagcga t tcacagatg | 1200 |
| tctgcctgtt catccgcgtc cagctcgttg agtttctcca gaagcgttaa t gtctggctt | 1260 |
| ctgataaagc gggccatgtt aagggcggtt ttttcctgtt tggtcacttg a tgcctccgt | 1320 |
| gtaagggga atttctgttc atgggggtaa ttgataccga tgaaacgaga g aggatgctc | 1380 |
| acgatacggg ttactgatga tgaacatgcc cggttactgg aacgttgtga g ggtaaacaa | 1440 |
| ctggcggtat ggatgcggcg ggaccagaga aaaatcactc agggtcaatg c cagcgcttc | 1500 |
| gttaatacag atgtaggtgt tccacagggt agccagcagc atcctgcgat g cagatccgg | 1560 |
| aacataatgg tgcagggcgc tgacttccgc gtttccagac tttacgaaac a cggaaaccg | 1620 |
| aagaccattc atgttgttgc tcaggtcgca gacgttttgc agcagcagtc g cttcacgtt | 1680 |
| cgctcgcgta tcggtgattc attctgctaa ccagtaaggc aaccccgcca g cctagccgg | 1740 |
| gtccgctctc ccttatgcga ctcctgcatt aggaagcagc ccagtagtag g ttgaggccg | 1800 |
| ttgagcaccg ccgccgcaag gaatggtgca tgcaaggaga tggcgcccaa c agtccccg | 1860 |

-continued

```
gccacggggc ctgccaccat acccacgccg aaacaagcgc tcatgagccc g aagtggcga    1920 gcccgatctt ccccatcggt gatgtcggcg atataggcgc cagcaaccgc a cctgtggcg    1980 ccggtgatgc cggccacgat gcgtccggcg tagaggatcc cgcgaaatta a tacgactca   2040 ctatagg                                                              2047
```